US012594437B2

(12) United States Patent
Naqa et al.

(10) Patent No.: US 12,594,437 B2
(45) **Date of Patent: \*Apr. 7, 2026**

(54) COMBINED RADIATION ACOUSTICS AND ULTRASOUND FOR RADIOTHERAPY GUIDANCE AND CANCER TARGETING

(71) Applicant: THE REGENTS OF THE UNIVERSITY OF MICHIGAN, Ann Arbor, MI (US)

(72) Inventors: Issam El Naqa, Ann Arbor, MI (US); Xueding Wang, Ann Arbor, MI (US); Paul Carson, Ann Arbor, MI (US); Kyle Cuneo, Ann Arbor, MI (US); Jean Moran, Ann Arbor, MI (US); Wei Zhang, Ann Arbor, MI (US); Ibrahim Oraiqat, Ann Arbor, MI (US)

(73) Assignee: THE REGENTS OF THE UNIVERSITY OF MICHIGAN, Ann Arbor, MI (US)

( \* ) Notice: Subject to any disclaimer, the term of this patent is extended or adjusted under 35 U.S.C. 154(b) by 0 days.

This patent is subject to a terminal disclaimer.

(21) Appl. No.: 18/883,578

(22) Filed: Sep. 12, 2024

(65) Prior Publication Data

US 2025/0001211 A1    Jan. 2, 2025

Related U.S. Application Data

(63) Continuation of application No. 17/600,564, filed as application No. PCT/US2020/032385 on May 11, 2020, now Pat. No. 12,102,843.

(Continued)

(51) Int. Cl.
| | |
|---|---|
| *A61N 5/10* | (2006.01) |
| *A61B 8/00* | (2006.01) |
| *A61B 8/08* | (2006.01) |

(52) U.S. Cl.
CPC .............. *A61N 5/1067* (2013.01); *A61B 8/08* (2013.01); *A61B 8/485* (2013.01); *A61N 5/1038* (2013.01);

(Continued)

(58) Field of Classification Search
None
See application file for complete search history.

(56) References Cited

U.S. PATENT DOCUMENTS

| | | | |
|---|---|---|---|
| 4,385,634 A | 5/1983 | Bowen | |
| 6,398,710 B1 | 6/2002 | Ishikawa et al. | |

(Continued)

OTHER PUBLICATIONS

Berlin et al., Phase 2 trial of guideline-based postoperative image guided intensity modulated radiation therapy for prostate cancer: Toxicity, biochemical, and patient-reported health-related quality-of-life outcomes. Pract Radiat Oncol, 2015. 5(5): e473-82. [Abstract Only].

(Continued)

*Primary Examiner* — Colin T. Sakamoto
(74) *Attorney, Agent, or Firm* — MARSHALL, GERSTEIN & BORUN LLP

(57) ABSTRACT

A method and system for performing online adapted radiotherapy are provided using combined ultrasound and ionizing radiation induced acoustic imaging (iRAI) computed tomography imaging techniques that can be used for measurement of low to ultrahigh dose deliveries (>40 Gy/s). Multiplexed transducers detect US and iRAI signals allowing for anatomical/functional imaging and radiation mapping with absolute dosimetry measurements of a region of interest during a radiotherapy session. Corrections to radiation dosage intensities and locations is determined and provided as feedback to a radiation source to improve the accuracy of applied radiation dosages intra- or inter-radiotherapy treatment sessions preventing the irradiation of (Continued)

healthy tissues and ensuring the accurate delivery of radiation to a tumor or region of interest.

17 Claims, 23 Drawing Sheets

Related U.S. Application Data

(60) Provisional application No. 62/845,437, filed on May 9, 2019.

(52) U.S. Cl.
CPC ......... *A61N 5/1039* (2013.01); *A61N 5/1049* (2013.01); *A61N 5/1071* (2013.01); *A61N 2005/1054* (2013.01); *A61N 2005/1058* (2013.01)

(56) References Cited

U.S. PATENT DOCUMENTS

| | | | |
|---|---|---|---|
| 7,662,097 | B2 | 2/2010 | Falco et al. |
| 8,600,003 | B2 | 12/2013 | Zhou et al. |
| 8,834,369 | B2 | 9/2014 | Magee |
| 9,144,403 | B2 | 9/2015 | Duric et al. |
| 9,314,160 | B2 | 4/2016 | Adler, Jr. et al. |
| 9,545,527 | B2 | 1/2017 | Moskvin et al. |
| 10,080,910 | B2 | 9/2018 | Bharat et al. |
| 2004/0122493 | A1 | 6/2004 | Ishibashi et al. |
| 2005/0197564 | A1 | 9/2005 | Dempsey |
| 2012/0165652 | A1 | 6/2012 | Dempsey |
| 2014/0020469 | A1 | 1/2014 | Gessert et al. |
| 2016/0184608 | A1 | 6/2016 | Adler, Jr. et al. |

OTHER PUBLICATIONS

Bol et al., Fast online Monte Carlo-based IMRT planning for the MRI linear accelerator. Phys Med Biol, 2012. 57(5):1375-85.

Bowen et al., Observation of ultrasonic emission from edges of therapeutic x-ray beams. Phys Med Biol, 1991. 36(4): 537-9.

Chen et al., Helical tomotherapy for radiotherapy in esophageal cancer: a preferred plan with better conformal target coverage and more homogeneous dose distribution. Med Dosim, 2007. 32(3):166-71.

Cooper et al., Chemoradiotherapy of locally advanced esophageal cancer: long-term follow-up of a prospective randomized trial (RTOG 85-01). Radiation Therapy Oncology Group. JAMA, 1999. 281(17):1623-7.

Datta et al., Local hyperthermia combined with radiotherapy and-/or chemotherapy: recent advances and promises for the future, Cancer Treat Rev., 41(9):742-53 (2015).

Eisenhauer et al., New response evaluation criteria in solid tumours: revised RECIST guideline (version 1.1). Eur J Cancer, 2009. 45(2):228-47.

Freedman et al., T2-Weighted 4D Magnetic Resonance Imaging for Application in Magnetic Resonance-Guided Radiotherapy Treatment Planning. Invest Radiol, 2017. 52(10):563-573.

Greaves, Evolutionary determinants of cancer. Cancer Discov, 2015. 5(8):806-20.

Hickling et al., Experimental evaluation of x-ray acoustic computed tomography for radiotherapy dosimetry applications, Med. Phys., 44(2):608-17 (2017).

Hickling et al., Ionizing radiation-induced acoustics for radiotherapy and diagnostic radiology applications, Med. Phys., 45(7):e707-e721 (2018).

Hickling, Feasibility of x-ray acoustic computed tomography as a relative and in vivo dosimeter in radiotherapy applications, Thesis Submitted to McGill University, Nov. 2014.

Higuchi et al., Current management of esophageal squamous-cell carcinoma in Japan and other countries. Gastrointest Cancer Res, 2009. 3(4):153-61.

Hsiao et al., Dual-wavelength photoacoustic technique for monitoring tissue status during thermal treatments, J. Biomed. Opt., 18(6):067003 (2013).

International Application No. PCT/US20/32385, International Search Report and Written Opinion, mailed Aug. 7, 2020.

Kilburn et al., Image guided radiation therapy may result in improved local control in locally advanced lung cancer patients. Pract Radiat Oncol, 2016. 6(3):e73-80.

Lawrence et al., Radiation dose-volume effects in the brain, Int J Radiat Oncol Biol Phys, 76 (3 Suppl):S20-7 (2010).

Lei et al., Toward in vivo dosimetry in external beam radiotherapy using x-ray acoustic computed tomography: a soft-tissue phantom study validation, Med. Phys., 45(9):4191-200 (2018).

Li et al., Different radiation treatment in esophageal carcinoma: a clinical comparative study. J Buon, 2012. 17(3):512-6.

Mallory et al., Therapeutic hyperthermia: The old, the new, and the upcoming, Crit Rev Oncol Hematol., 97:56-64 (2016).

Mascarenhas et al., A photoacoustical radiation dosimeter. Med Phys, 1984. 11(1):73-4.

McGranahan et al., Clonal Heterogeneity and Tumor Evolution: Past, Present, and the Future. Cell, 2017. 168(4):613-628.

Miller et al., Cancer treatment and survivorship statistics, 2016. CA Cancer J Clin, 2016. 66(4):271-89.

Minsky et al., Final report of Intergroup Trial 0122 (ECOG PE-289, RTOG 90-12): Phase II trial of neoadjuvant chemotherapy plus concurrent chemotherapy and high-dose radiation for squamous cell carcinoma of the esophagus. Int J Radiat Oncol Biol Phys, 1999. 43(3): 517-23.

Minsky et al., INT 0123 (Radiation Therapy Oncology Group 94-05) phase III trial of combined-modality therapy for esophageal cancer: high-dose versus standard-dose radiation therapy. J Clin Oncol, 2002. 20(5):1167-74.

Oraiqat et al., An ionizing radiation acoustic imaging (iRAI) technique for real-time dosimetric measurements for FLASH radiotherapy, Med. Phys., 47(10):5090-101 (2020).

Osuka et al., Overcoming therapeutic resistance in glioblastoma: the way forward, J. Clin. Invest., 127(2):415-26 (2017).

Rao et al., A review of hyperthermia combined with radiotherapy/chemotherapy on malignant tumors, Crit. Rev. Biomed. Eng., 38(1):101-16 (2010).

Schmidt et al., Radiotherapy planning using MRI. Phys Med Biol, 2015. 60(22):R323-61.

Scott et al., A genome-based model for adjusting radiotherapy dose (GARD): a retrospective, cohort-based study. Lancet Oncol, 2017. 18(2):202-211.

Shahzadeh et al., Evaluation of normal lung tissue complication probability in gated and conventional radiotherapy using the 4D XCAT digital phantom, Comput. Biol. Med., 97:21-29 (2018).

Tian et al., Imaging and sensing based on dual-pulse nonlinear photoacoustic contrast: a preliminary study on fatty liver, Optics Letters., 40(10):2253-6 (2015).

Watson et al., Engineered Swine Models of Cancer, Front. Genet., 7:78 (2016).

West et al., Genetics and genomics of radiotherapy toxicity: towards prediction. Genome Med, 2011. 3(8):52.

Xact Robotics Ltd., Evaluation of the Safety, Effectiveness & Usability of the XACT Robotic System for Image Guided Percutaneous Procedures, downloaded from the Internet at: <https://clinicaltrials.gov/ct2/show/NCT03008603?term=XACT&draw=3> (posted Jan. 2, 2017).

Zhu et al., Ultrasound Hyperthermia Technology for Radiosensitization, Ultrasound Med. Biol., 45(5):1025-43 (2019).

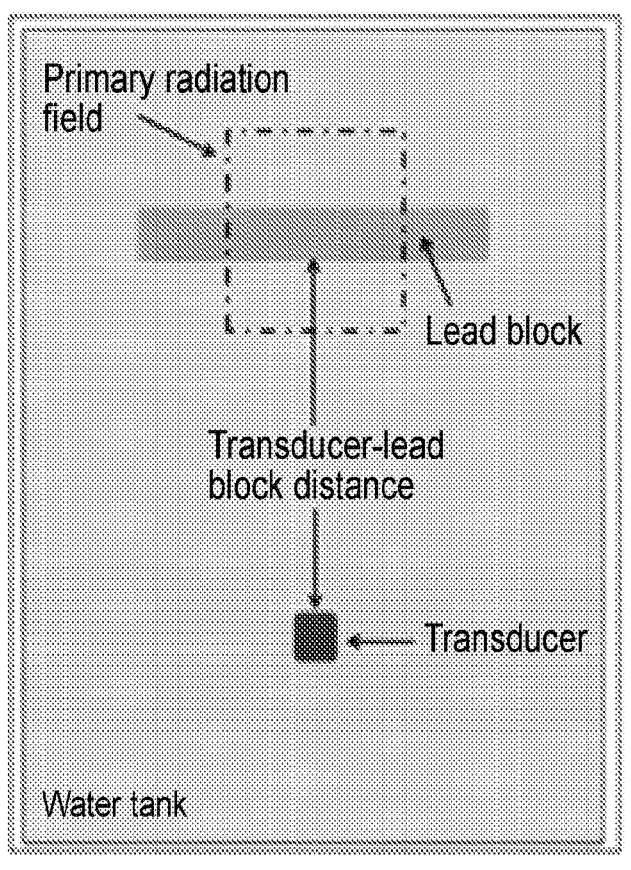
*FIG. 4A*
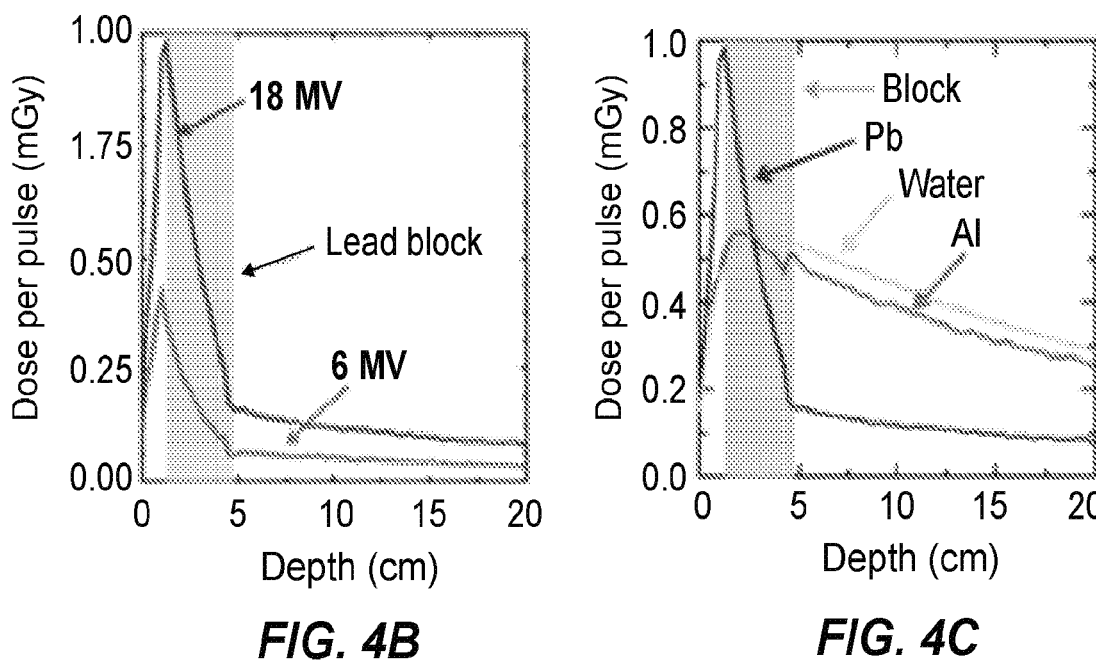
*FIG. 4B*                    *FIG. 4C*

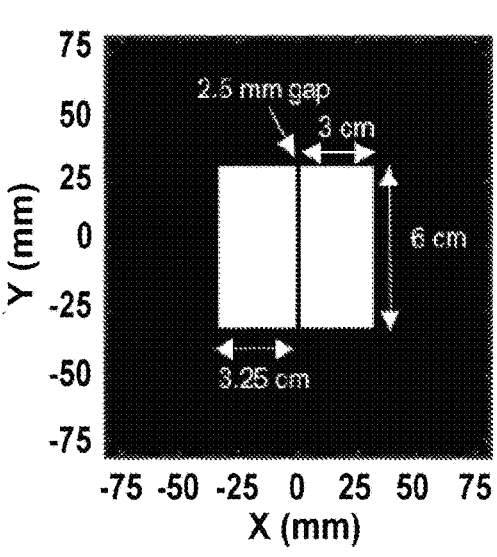
*FIG. 5A*
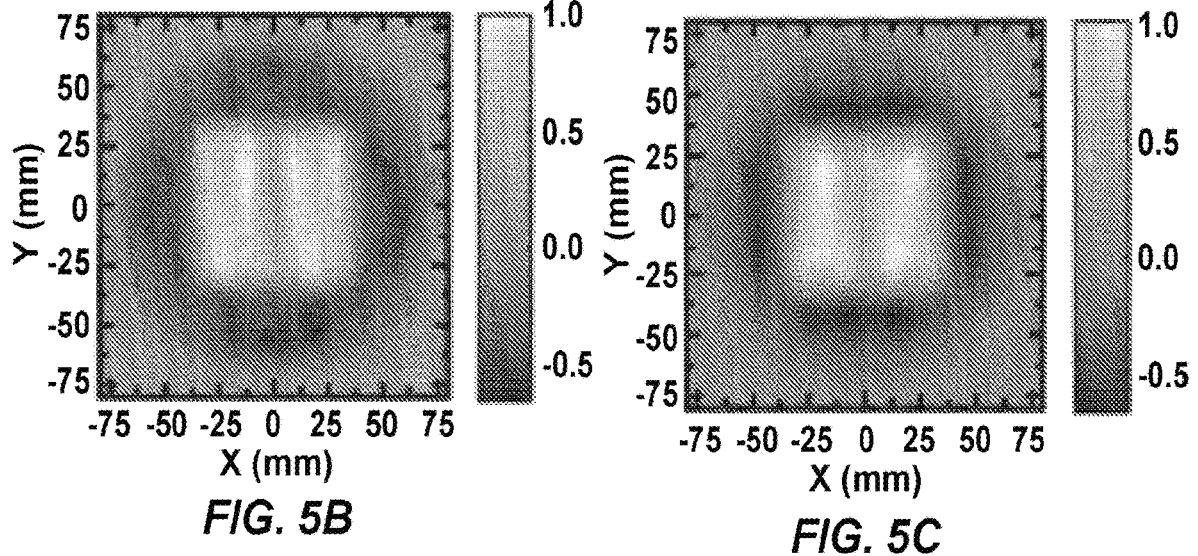
*FIG. 5B*
*FIG. 5C*
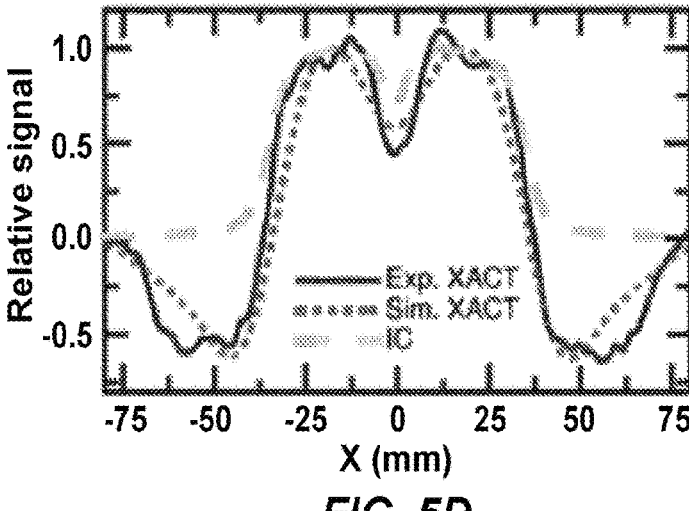
*FIG. 5D*

XACT and EBT3 measurements for 15° physical wedge

XACT and EBT3 measurements for 30° physical wedge

XACT and EBT3 measurements for 45° physical wedge

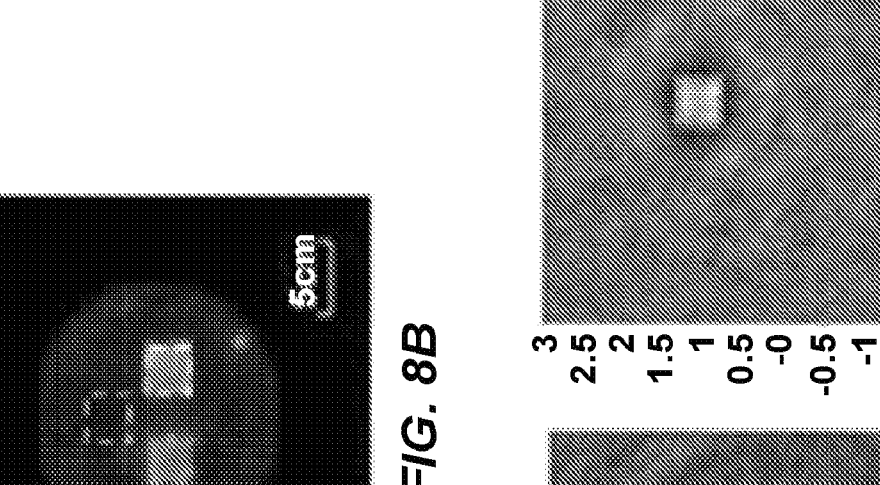
FIG. 8E
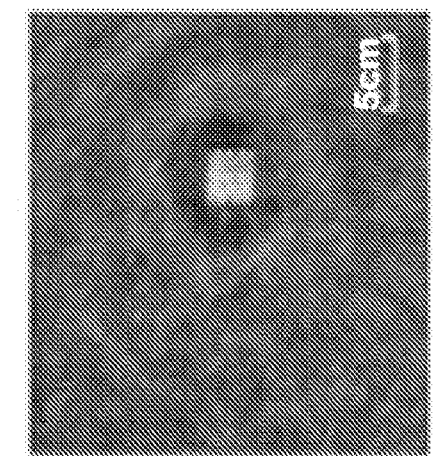
FIG. 8B
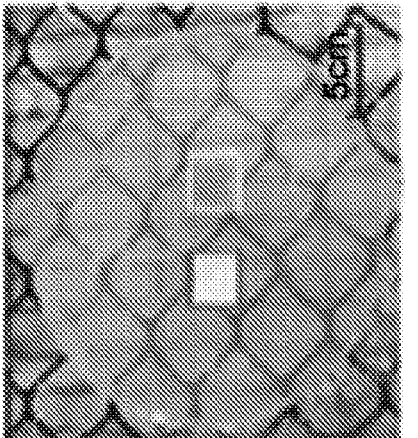
FIG. 8A
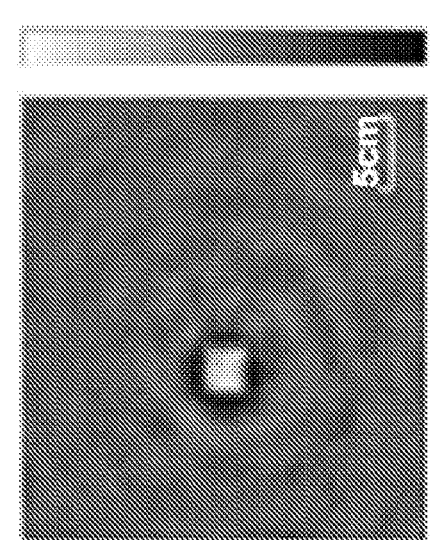
FIG. 8D
FIG. 8C

COMBINED RADIATION ACOUSTICS AND ULTRASOUND FOR RADIOTHERAPY GUIDANCE AND CANCER TARGETING

CROSS-REFERENCE TO RELATED APPLICATIONS

This application is a Continuation of U.S. application Ser. No. 17/600,564, filed Sep. 30, 2021, which claims the benefit of U.S. Provisional Application Ser. No. 62/845,437, filed May 9, 2019, the entirety of which are hereby incorporated herein by reference.

STATEMENT REGARDING FEDERALLY SPONSORED RESEARCH OR DEVELOPMENT

This invention was made with government support under CA222215 awarded by the National Institutes of Health. The government has certain rights in the invention.

FIELD OF DISCLOSURE

The present disclosure relates to radiation therapy dosimetry and anatomical imaging and, more specifically, to a feedback system necessary for monitoring delivered radiation dose and beam accuracy to adapt therapy online.

BACKGROUND

Radiotherapy (RT) is recognized to be a highly conformal and effective treatment for many types of cancers and is the primary treatment modality for many locally advanced cancers. However, the efficacy of RT is dependent on accurate localization of the tumor boundary and surrounding tissues at the time of radiation delivery. Discrepancies have been observed between planned and delivered radiation treatments, which reduces the amount of radiation delivered to the tumor, and undesirably increases the radiation delivered to healthy or normal tissues. In addition, the discrepancies between planned and delivered radiation are exacerbated due to accumulative setup errors and organ motion over the course of fractionated treatments, such as in the cases of liver and pancreatic cancers. Moreover, promising dose escalations in such cancers are limited by the risks of radiation-induced normal tissue toxicity. In particular, the success of ultrahigh dose-rate (FLASH) irradiation, which increases the therapeutic ratio (sparing normal tissue and eradicating tumor tissues), in preclinical study calls upon suitable technologies for safe delivery of such >40 Gy/s irradiation.

A feedforward process is commonly implemented when designing a patient's treatment plan, which may involve pre-treatment scans and imaging. Despite meticulous off-line treatment planning processes and on-board imaging, a major impediment to achieving RTs curative promise is the current delivery process, where the planned tumor area is exposed to fixed levels of ionizing radiation from a linear accelerator (linac) over time, irrespective of target deformations, organ motion, or function. The geometric uncertainties in a feedforward process are often accounted for through compensations such as increasing the planning margin around the tumor and pre-treatment daily setup adjustments. These compensations can result in unnecessary exposure of uninvolved tissue and the delivery of debilitating toxicities to healthy and normal tissues which results in inefficient tumor kill, and increased exposure of surrounding normal tissue causing detrimental radiation related injuries, particularly with new ultrahigh dose-rate deliveries.

Radiation planning and delivery methods from intensity modulated RT (IMRT), volumetric arc therapy (VMAT), and stereotactic body radiotherapy (SBRT) cases, necessitate more accurate and real-time volumetric in vivo dosimetry to ensure that the correct amount of dose is accurately delivered to the desired location. Although there exists a wide variety of methods for clinical dosimetry (e.g., ion chambers (ICs), diodes (single or array configurations), thermal/optical stimulated dosimeters, metal oxide semiconductor field effect transistors, plastic scintillators, electronic portal imaging devices, gels and films), these techniques are mostly limited to point measurements on the external surface of a patient. These dosimetry methods also lack the ability to conduct measurements that are volumetric, real-time, and independent of dose rate or energy. Newer dosimetry methods such as transit dosimetry (with a linac-independent device or an electronic portal imaging device) are not economically feasible for a typical radiation oncology clinic, or lack the necessary anatomical information.

SUMMARY

In accordance with an example, a method for online adapted radiotherapy comprises: positioning transducers configured to receive signals from a target site or region of interest; irradiating a target site or region of interest; receiving at transducers, ionizing radiation induced acoustic and ultrasound signals from the target site or region of interest; processing the received signals from the target site or region of interest; determining relative dosimetry imaging of the applied radiation; determining spatial imaging of tissue in the region of interest; determining a property of tissue structures in the region of interest; deriving absolute dosimetry imaging from the relative dosimetry imaging, spatial mapping, and property of tissue structures in the region of interest; fusing the absolute dosimetry imaging and the spatial imaging of the tissue; and providing feedback to a radiation source and updating parameters for a next radiation dosage.

In accordance with another example, a system for online adapted radiotherapy comprises: a radiation source configured to provide radiation to a region of interest; a transducer comprised of ionizing radiation induced acoustic transducer elements configured to receive ionizing radiation induced acoustic signals from the region of interest, and ultrasound transducer elements configured to receive ultrasound signals from the region of interest; a signal acquisition system configured to receive electrical signals from the transducer; and a processing system configured to (i) receive and process signals from the signal acquisition system, (ii) determine relative dosimetry images of a region of interest, (iii) determine tissue images and tissue properties of a region of interest, (iv) derive absolute dosimetry information of a region of interest, and (v) provide feedback to the radiation source with updated parameters for a next radiation dosage.

BRIEF DESCRIPTION OF THE DRAWINGS

FIGS. 4A-4C illustrate measured radiation acoustics in soft tissue and high-Z materials, in accordance an example.

FIGS. 5A-5D display experimental and simulated results of x-ray acoustic dosimetry with a dual-rectangle radiation dose pattern, in accordance an example.

FIGS. 8A-8E display x-ray acoustic computed tomography and ultrasound images of a phantom made of porcine gelatin embedded with both pig fat and muscle tissue, in accordance an example.

DETAILED DESCRIPTION

Figures 1A, 1B:
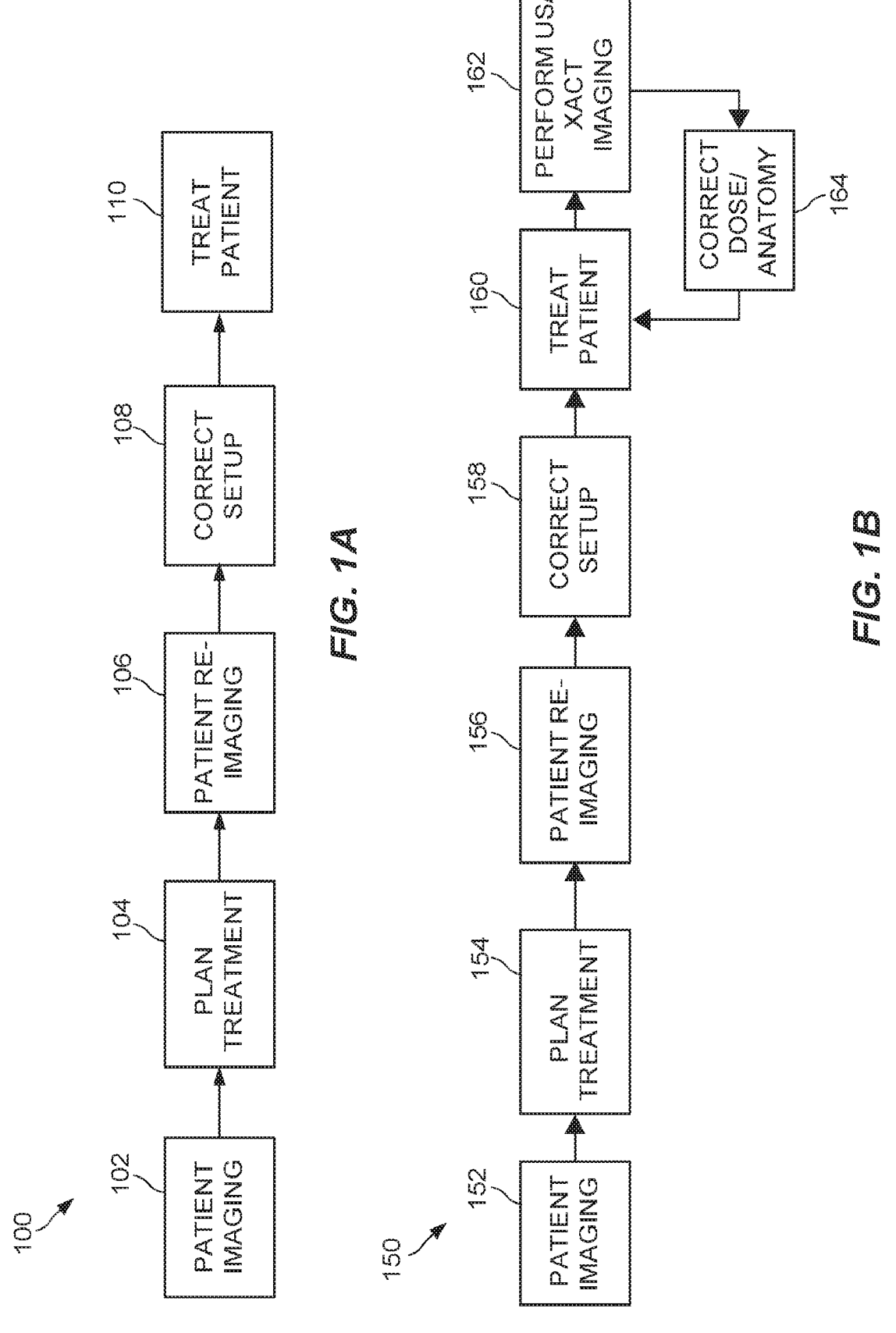
FIGS. 1A and 1B are block diagrams of a feedforward radiotherapy process and a feedback radiotherapy process, in accordance with examples herein.

The present technology includes methods and systems that provide nonionizing, noninvasive, real-time, and cost-effective combined dosimetry and imaging for online feedback in radiotherapy (RT) delivery for moderate and ultra-high dose-rate deliveries. Utilizing transducers that measure both ionizing radiation induced acoustics and ultrasound technologies, absolute dosimetry information and three-dimensional imaging of a region of interest (ROI) can be obtained. Results of simulations and trials have indicated that both imaging and dosimetry information are required to meet original treatment planning goals, as well as to account for changes during treatment or between treatment fractions. The system described herein can provide instantaneous feedback on tumor status and delivered radiation dose allowing recalibrating and adjusting of the applied radiation beam's geometries and intensity in real time to optimize RT delivery.

In some examples, the present techniques are able to exploit already present intrinsic radiation interaction properties for developing irradiation dose feedback systems. One such example is Ionizing radiation acoustic imaging (iRAI). iRAI is a medical imaging and real-time dosimetry modality that allows for such online in vivo deep tissue dosimetry. It has been long recognized that the rapid deposition of ionizing energy in a localized region within the irradiated object leads to a temperature rise and thermoelastic expansion, causing the induction of acoustic waves, which is known as the thermoacoustic effect. The acoustic waves have pressure amplitudes proportional to the amount of the radiation dose within the medium. Following the generation of an initial pressure distribution, the propagation of the resulting acoustic pressure waves can be described using a thermoacoustic wave equation. The propagating thermoacoustic waves generated by linear accelerator (linac) systems can be detected and information about the targeted tissue and radiation absorption, can be collected by ultrasound transducers located on the surface of the body around a region of interest. Since for a given tissue structure and beam geometry, the initial pressure is proportional to the energy deposited (i.e., radiation dose), both the beam location and the dosimetry information can be extracted from the detected pressure wave. An example form of iRAI provides x-ray radiation as the ionizing radiation, this type of dosimetry is called x-ray acoustic computed tomography (XACT). Typically, dosimetry for deep seated tumors requires invasive surgical procedures to implant point dosimeters, whereas the 3D detection of radiation-induced acoustic waves provided by iRAI, and more specifically XACT, offers a unique opportunity that can provide volumetric representation of the delivered dose in vivo at the tumor depth. Although iRAI and XACT are relative dosimetry measurements, tissue geometry and density information can be used in conjunction with iRAI and/or XACT measurements to determine an absolute dose conversion.

Ultrasound (US) is a 3D/4D noninvasive, safe, and real-time (typically, 10 to 30 frames/sec) anatomical and physiological imaging modality that has already established itself as a key tool for aiding diagnosis of cancers, and particularly, for abdominal (liver, stomach, pancreas) cancers and for image-guidance in RT. US may also be used for imaging and diagnosis of other types of cancer such as brain cancer. US is frequently used as a first-line diagnostic/surveillance tool for patients presenting with cirrhosis (high risk for hepatocellular carcinoma) or jaundice, or abdominal pain (high risk for pancreatic cancer). Although US is commonly used for diagnosis and feedforward therapy planning, it is not typically implemented in feedback systems for RT therapy since other technologies such as MRI-linac can provide better soft tissue discrimination but not dosage information. Implementing XACT dosimetry during RT can enable online monitoring of the delivered radiation dose absorbed by the tumor and its surrounding tissues by using clinical ultrasound with its high imaging speed, low cost, portability, and its nonionizing and noninvasiveness advantages.

The present techniques, combining XACT and US measurements to assess dosing for low and ultrahigh dose rate delivery, provide a number of key advantages over conventional systems for RT and dosimetry for various target sites (e.g., brain, liver, kidney, or any other biological ROI).

In various examples, an advantage is that the present techniques can determine tissue properties in the ROI and relative dosing to the ROI. For example, Relative dosage information in a ROI can be derived from measured XACT signals during RT. Spatial imaging and tissue mapping in the region of interest can be obtained using computed tomography (CT) or US measurements to determine where different tissues are and what kinds of tissues are present. For example, US measurements may be used to determine where a tumor is relative to other healthy tissues such as a nearby organ, bone, or other tissue structure. Separately, beam forming can be performed on the XACT information to determine the directivity of the received XACT signal providing a spatial mapping of the radiation dosage in the ROI. The spatial tissue mapping and the mapping of the radiation dosage can then be combined or fused to provide information of how much radiation the various tissues in the ROI received.

In various examples, another advantage is that the present techniques can determine an absolute radiation dosage. Non-invasive XACT is a relative measurement due to the absence of any absolute measurements of radiation at the tissue sites in the ROI. Using CT or US to determine tissue properties in the region of interest can include information such as various tissue density's or density gradients due to various types of tissues in a ROI. The attenuation of radiative signals, such as XACT signals, can be determined by the densities of tissues that the radiation propagates through. Therefore tissue density information can be used to back-propagate an XACT signal to a tissue site in the ROI to determine the absolute value of the applied radiation in the ROI. US can also be used to determine the spatially distributed speed of sound, which may assist in determining the absolute value of the applied radiation in the ROI. Additional information such as stress and/or strain properties in the ROI may also assist in determining absolute XACT dosimetry. Each pixel of a US/XACT measurement may require independent back propagation due to variations and inhomogeneity of tissue in a ROI to determine the absolute applied radiation dosage for an entire ROI.

The disclosed system and methods combine XACT dosimetry and US anatomical imaging in ways that enable real-time measurements of delivered radiation dose, what we term herein real-time dosimetry. The combined US/XACT measurements resulting from the techniques herein may then be used for optimizing tumor targeting during RT therapy. The present techniques are able to provide less harmful, more cost effective alternatives to fluoroscopic imaging and integrated MRI linac systems, which can be costly for the typical oncology clinic. In addition, the combined US/XACT techniques herein are able to provide in vivo dosimetry within the irradiation risk of conventional techniques such as CT scans, and can more accurately measure risky but promising ultrahigh dose rate delivery where traditional dosimeters underperform.

In some examples, the present techniques are applied to FLASH radiotherapy (FLASH-RT) providing the ability to have real-time measurements during a therapy session. FLASH-RT is an ultra-high dose rate (>40 Gy/s) radiotherapy orders of magnitude higher than conventional dose rates (~0.1 Gy/s). FLASH-RT has the ability to increase the differential effect between normal tissue and tumors, which has shown improvements in the therapeutic ratio by at least 20-30% in in vivo systems. FLASH dose rates have shown that skin toxicities are reduced in mini-pigs and toxicities (e.g., mucositis and depilation) are reduced in cats being treated for squamous cell carcinoma of the nasal planum, with no severe late skin fibronecrosis observed using FLASH. FLASH-RT has successfully been performed on patients with cutaneous lymphoma with a 15 Gy FLASH-RT in 90 ms with minimal side effects, demonstrating the potential of FLASH-RT but also its current limitation as a surface-based RT. Currently, methods for monitoring the spatial application and amount of a FLASH-RT dose are limited, and there no methods for real-time in-vivo dosimetry during a FLASH-RT session. Additionally, most techniques for performing dosimetry during convention RT are not feasible for FLASH-RT due to the high dose rate applied during FLASH-RT.

A common radiation detector implemented in RT dosimetry is an ionization chamber (IC). Employing ICs at the ultra-high FLASH dose rates can become problematic due to the decreasing ion collection efficiency with increasing dose per pulse, requiring the use of an empirical model for additional dose correction factors. As an alternative, film may be implemented in high dose rate dosimetry, as film may be dose rate independent and can be placed directly on the surface of the patient. However, film is not a real-time measurement which is better suited for quality assurance of the treatment plan rather than in vivo measurements and treatment calibration. Other dosimetry methods may be used for FLASH-RT, but they are typically limited to surface measurements and do not allow for any real time feedback, dose measurements in deep tissue, or for the measurement of the treatment volume for each linac pulse. Therefore, for clinical implementations of FLASH-RT, it is desirable to quantify the deposited dose for individual linac pulses at the treatment volume at depth, as opposed to only performing surface measurements. In addition, it may also be beneficial to register a dose with the patient's anatomy to ensure that the radiation is applied and deposited accurately and safely at the intended target in real-time, which is not possible with current clinical dosimetric techniques for conventional or FLASH-RT. The present techniques, however, are able to overcome the drawbacks of current dosimetric and applied radiation monitoring techniques by combining both US and iRAI information to determine a dosage amount and region of an applied dosage for conventional and FLASH-RT. Although described herein for conventional and FLASH-RT, the present techniques can be applied to other forms or RT for performing real-time dosimetry and dosage mapping for providing feedback and tuning during an RT therapy session.

FIGS. 1A and 1B are flow diagrams of a conventional feedforward RT treatment method 100, according to prior art, and a feedback RT treatment method 150 in accordance with the present techniques are shown, respectively.

Before a therapy session, the target site or region of a patient is imaged at blocks 102 and 152, respectively. The initial patient images are analyzed and a patient therapy plan is determined, blocks 104 and 154, respectively. When the therapy session is about to commence a patient may be reimaged, at blocks 106 and 156 respectively, the physical setup and planned therapy may be adjusted or corrected, at blocks 108 and 158 respectively, and the patient is then treated, at block 110 and 160 respectively. With feedforward RT systems, e.g., implementing method 100, no further tuning or correcting of the radiation beam is performed during the therapy session. The feedback RT treatment method 150, however, further includes obtaining US/XACT images, at block 162, and using that image information to correct the dose intensity and anatomy, at block 164. The feedback provided by the US/XACT imaging allows for online correction of radiation dosages which may reduce incongruities between planned and delivered radiation dosages to a target site or region, and reduce the amount of radiation delivered to healthy or normal tissue.

Figure 2:
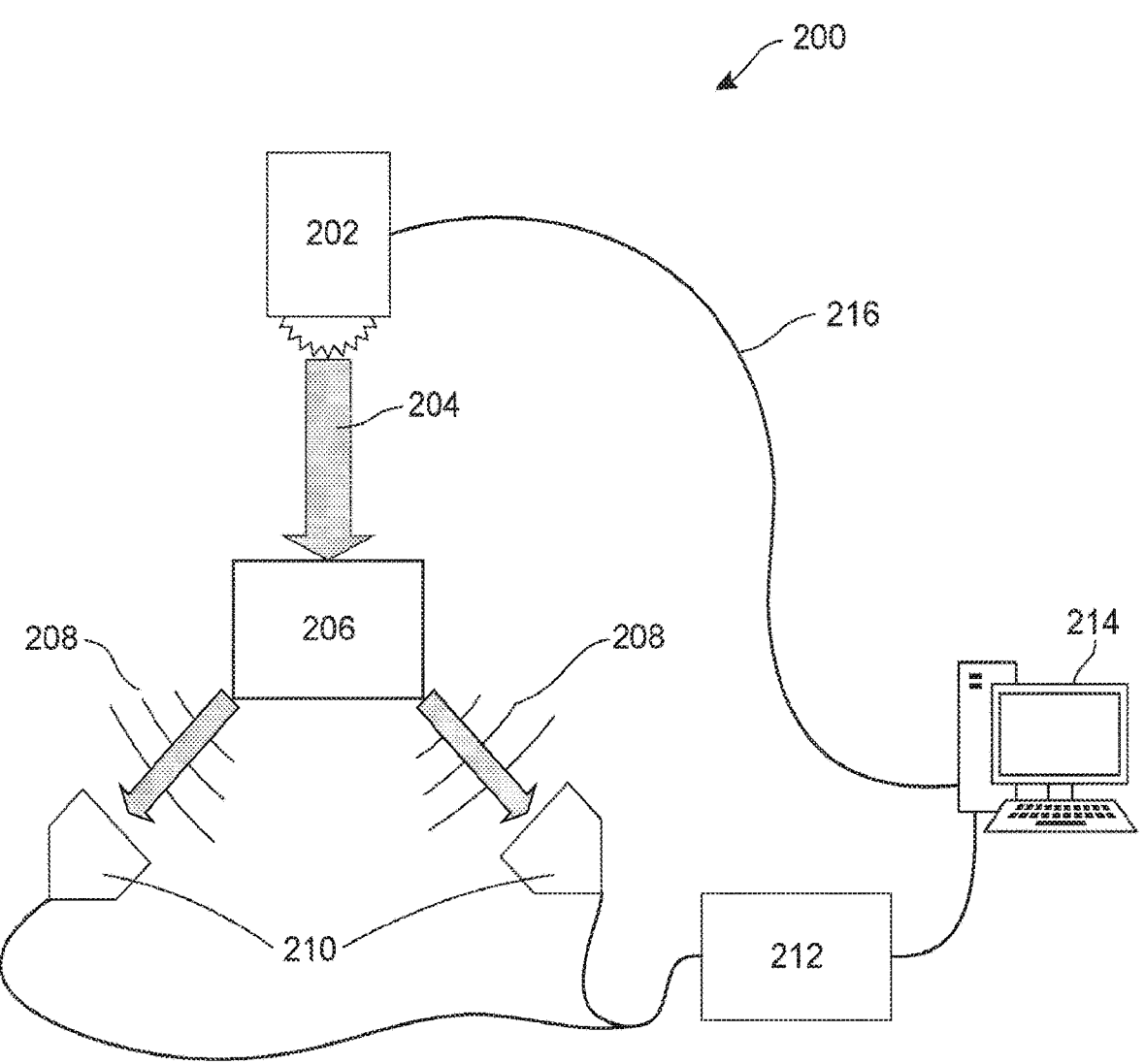
FIG. 2 illustrates an example joint feedforward x-ray acoustic computed tomography and ultrasound imaging radiotherapy system, in accordance an example.

FIG. 2 illustrates a US/XACT system 200. In the US/XACT system 200 of FIG. 2, a sample or region of interest (ROI) 206 is treated with a radiation beam 204 by a radiation source 202. In some examples, the sample 206 is of a patient and may be an organ or tissue or any portion of the subject to receive in vivo radiation treatment. In some examples, the sample 206 is treated ex vivo. The sample 206 may be organic or non-organic, a biological sample, or a non-biological sample. For example, the sample 206 may be a container, such as a water tank, with suspended materials inside, a gel construction for medical testing in a laboratory, or any other material of interest. A water tank or a gel construction may be useful for medical testing of planned RT treatment using US/XACT treatment plans, or for calibrating a specific US/XACT device and any processing algorithms.

During operation, the radiation beam 204 is applied and two multiplexed XACT/US transducers 210 capture images of a ROI of the sample 206. In the illustrated example, multiple transducers 210 are used to each scan the ROI. The respective scans may be spatially combined or used independently. The transducers 210 provide image data to a signal acquisition system 212 through an electrical connection 216 which can then send the US/XACT information to a processor 214. The reconstructed 3D-XACT/US images may be presented on a console or processed and further analyzed in software.

In some examples, the transducers 210 are dual mode transducers that contain both US and XACT transducer elements and are configured to simultaneously detect US and XACT signals. The dual mode nature of the transducers may be achieved in many different ways, e.g., using different configurations transducer elements.

Figure 3A:
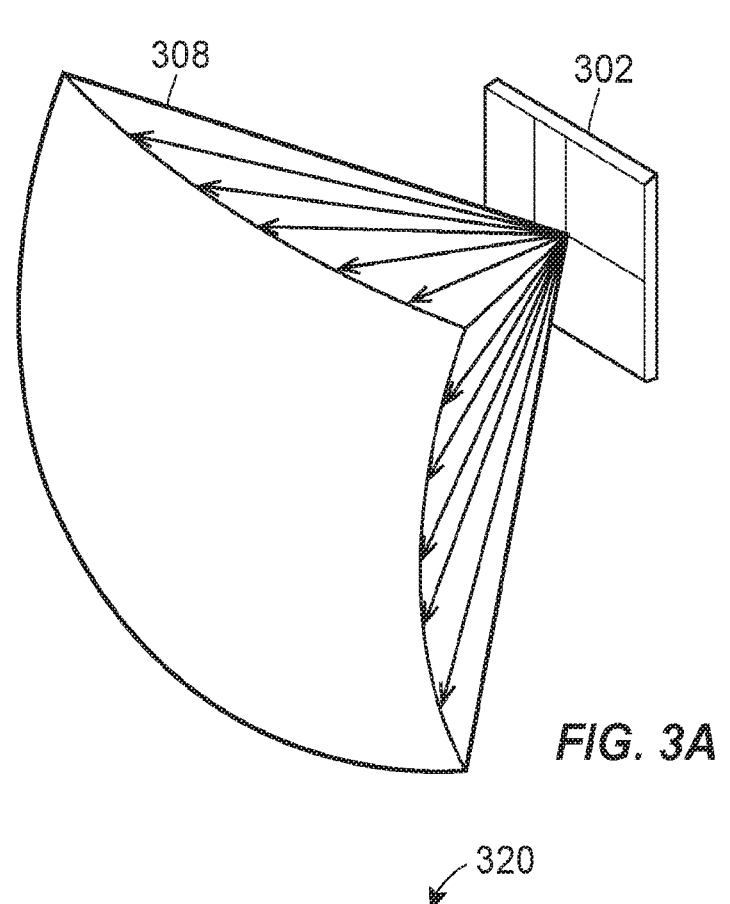
FIG. 3A illustrates an example joint ultrasound and x-ray acoustic computed tomography matrix array transducer, in accordance an example.

In an example, the transducers 210 may be configured as matrix array transducers (MATs), such as MAT 302 illustrated in FIG. 3A. The MAT 302 is a two-dimensional array of transducer elements configured to receive signals from a particular region of interest corresponding to a field of view (FOV) 308. The MAT 302 is able to perform volumetric imaging over the FOV 308, as illustrated in FIG. 3A, for example. In various examples, the MAT 302 has a wider FOV and higher resolution than conventional phased/linear array counterparts.

Figure 3B:
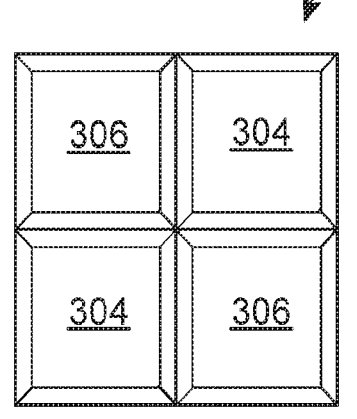
FIGS. 3B and 3C depict various examples of matrix array transducers having different arrangements of x-ray acoustic and ultrasound transducer elements, in accordance an example.
Figure 3C:
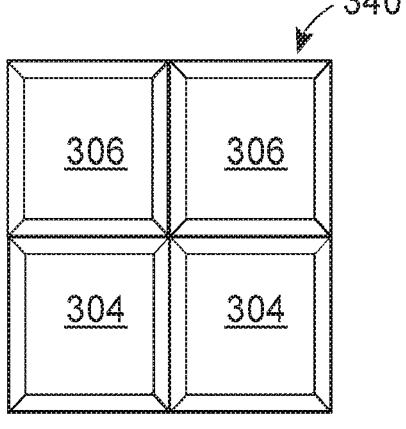

In an embodiment, such as the embodiments 320 and 340 of FIGS. 3B and 3C, the transducer may be a 32×32 array of XACT transducer elements 304 and US transducer elements 306, for 1024 total elements. For example, the MATs 320 and 340 may have 512 XACT transducer elements 304 and 512 US transducer elements 306. XACT transducer elements 304 and US transducer elements 306 may be in spatially different regions of the transducer, as illustrated by the checkered pattern arrangement of the embodiment 320 of FIG. 3B. MATs with a checkered arrangement of XACT transducer elements 304 and US transducer elements 306 provide control over the spatial tuning of a received signal in two perpendicular angles (azimuth/elevation) and allow the reception of signals from an entire volume in one pass.

In other embodiments, such as the embodiment 340 of FIG. 3C, the transducer elements may be arranged in parallel subgroup arrays with US transducer elements 306 across an upper portion of the transducer embodiment 340, and XACT transducer elements 304 across a lower portion of the transducer embodiment 340. Other transducer element arrangements, such as interleaving transducer elements, forming smaller groupings of UV or XACT transducer elements, vertical parallel strips of transducer elements, higher resolution checkered patterns, higher resolution parallel groupings, or any other configuration of XACT and US elements may be implemented for the transducer elements to receive an XACT and/or US signal from a region of interest. Each transducer element may have the same size. In some examples, each US transducer element may have the same size and each XACT transducer element may have the same size, but the transducer elements may be different between each of these two groups.

The desired arrangement of transducer elements may depend on a desired image resolution, a desired FOV overlap for error mitigation, a desired image depth, the size and/or shape of a target site or region of interest, and/or the body part or region of a patient to be observed, among other factors. In embodiments, the MATs may also be comprised of 144 elements, 256 elements, 900 elements, 1600 elements, 2500 elements, or any other number of elements desired to achieve a suitable FOV, signal to noise ratio (SNR), and/or resolution for a given application, among other factors. Even though MATs have been proposed as the XACT/US transducer, an alternative technology for 3D imaging is the application of piezoelectric micro-machined ultrasound transducers (PMUTs), which can be attached to the patient body surface, e.g., as a belt, ensuring coverage of a region of interest. In addition to MATs and PMUTs, any other transducer technology suitable for XACT/US measurements may be implemented in embodiments.

In embodiments, the signal acquisition system 212 of FIG. 2 may be a commercial research platform such as one provided by Verasonics Inc. A Verasonics system in combination with MATs allows for simultaneous acquisition of B-mode US images presenting the tissue structures (including temporal localization of the tumor and sensitive normal tissues) and XACT images, demonstrating the radiation dose, that can be displayed at, or almost at, the same time. The images can be displayed either side-by-side or as a fused image on a screen, facilitating the modulation of radiation beam position, shape, and intensity during real-time delivery. In embodiments, the signal acquisition system 212 of FIG. 2 may allow for the integration of customized transducer arrays and compatibility with universal transducer adaptors (UTAs), such as is provided by a Verasonics Inc., Vantage 256 system. In addition, the signal acquisition system 212 may allow for the development of novel beam forming techniques, flexible software interfaces, integration with MATLAB and/or other coding platforms, provide signal gain, high-speed acquisitions, or any other processing ability desired before the image data is sent to a processor. The signal acquisition system 212 system will be used herein for descriptions of embodiments for clarity and is not the only signal acquisitions system 212 able to perform the required operations for a XACT/US imaging system. In fact, non-commercial custom systems may also be implemented for any XACT/US signal acquisition system 212.

The signal acquisition system 212 may include MATs from 256 to 2048 independently controlled channels with access to the RF data from each channel. In the illustrated example, the signal acquisition system 212 of FIG. 2 drives two 1024-element 2D MATs as the transducers 210 with 8-1 multiplexing using a single signal acquisition system 212 or 4-1 multiplexing using two signal acquisition systems. The multiplexer may switch the active channels of the beamformer to the transducers 210. In embodiments, the center frequency of the transducers 210 is 1.0 MHz, which is a compromise between a standard XACT operating frequency of 500 kHz and a clinical US imaging system which has typical center frequencies greater than 2 MHz. In embodiments, the center frequency of the transducers 210 may have a −20-dB bandwidth of about 110% to provide highly sensitive detection, and to facilitate imaging with satisfactory image quality and penetration. In preferred embodiments, each transducer 210 is about 2.6×2.6 cm$^2$ in dimension with a 0.5λ pitch. When the targeted imaging depth is 5 cm, the expected axial and lateral resolutions for B-mode XACT/US are about 1.5 mm and 3.7 mm, respectively. In addition, different sub-array configurations (checkered, parallel, etc.) can be multiplexed for B-mode US and XACT to achieve a desired FOV and spatial image resolution. The location of the US/XACT 210 transducers may be patterned to obtain adequate 3D dosimetry and physiological images.

In examples, the transducers 210 may be maintained in a fixed position during a treatment session, as illustrated in FIG. 2, or the transducers 210 may be dynamic with spatial motion relative to a target site, ROI, or sample 206. In a dynamic embodiment, a single transducer may rotate around a ROI which may reduce the number of transducers required for imaging, although, it may also slow down the rate of imaging. In yet other embodiments, the transducers 210 may rotate around or shift laterally in relation to a ROI to take images at different angles or positions. Multiple images from different angles may be compounded, or combined, to provide highly reliable 3D reconstructions of dosimetry and anatomical information compared to images generated from the single position, angle, and FOV of a statically positioned transducer 210.

During patient simulation, the proper positioning of MATs may be determined using CT imaging. Factors to consider when determining proper probe positioning include ensuring that the probe does not interfere with the RT beam, the optimal FOV of a ROI, proper distance to receive enough US/XACT signal strength for desired image SNR, resolution, and image quality, among other factors. The optimality of the determined FOV can be verified by taking an US image prior to irradiation.

Perineal placement, between the legs of a patient or subject, of one of the two transducer arrays, may act as a compromise between angle of viewing and distance to improve image quality depending on the ROI. If bones or gas obstruct part of the aperture of any array, the obstructed elements may be turned off. The use of two MATs with multiplexed US/XACT channels by a signal acquisition system 212 system provides physically co-registered 3D images and high flexibility for optimizing FOV. Perineal positioning is may also minimize possible interference with the RT beam or the current clinical workflow. In other embodiments, the positions of the two arrays at the side or sides of a patient can be easily adjusted to enable a good coverage of the target ROI and allow for spatial compounding.

FIGS. 4A and 4B display experimental data that demonstrates various capabilities of a combined US/XACT imaging system. A clinical linac system was used to radiate a water tank containing various materials including lead, aluminum, bone, and/or water. An US transducer measured the radiation acoustics generated by the different materials suspended in the water tank at various depths, and with various applied radiation beam energies. It was observed that the measured signal was not only detectable in high Z materials, observed in FIG. 4A, but also in soft tissue-like materials as in FIG. 4B demonstrating the feasibility of using such a method to measure signals in tissues in a ROI of a patient.

FIGS. 5A-5D display experimental results of an applied dual rectangular radiation dose pattern, shown in FIG. 5A. FIG. 5B shows the measured dosage from a triggered linac pulse as the radiation source, determined using XACT measurements in water with a transducer at 320 angular steps. A practical simulation of the experiment is presented in FIG. 5C with high agreement between the experimental (FIG. 5B) and simulated results. FIG. 5D presents ion chamber (IC) measurement profiles of the applied radiation along the x-axis. Main errors due to the loss of signal in XACT are primarily caused by the limited 64% fractional bandwidth by the transducer used in the measurements of FIGS. 5A-5D. This limit was confirmed by simulations using 100%-120% bandwidth transducers.

Figure 6A:
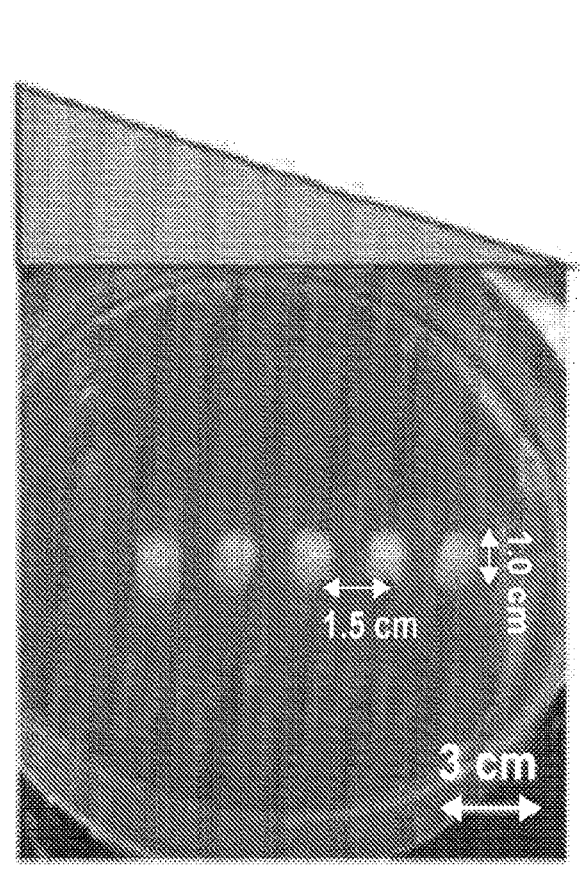
FIG. 6A-6C illustrate the sensitivity and dose uncertainties of x-ray acoustic computed tomography utilizing irradiated phantoms at various wedge angles, in accordance an example.
Figure 6B:
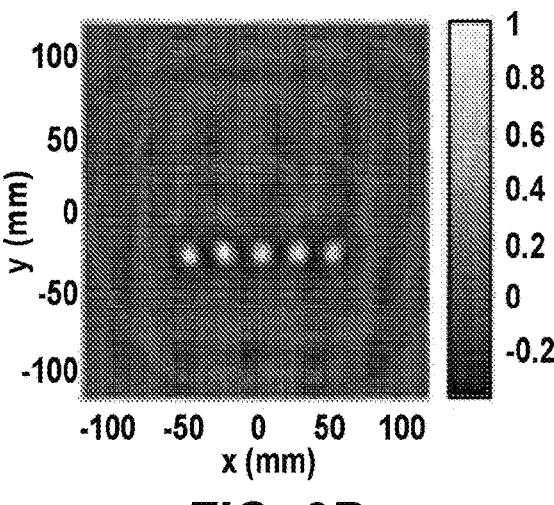
Figure 6C:
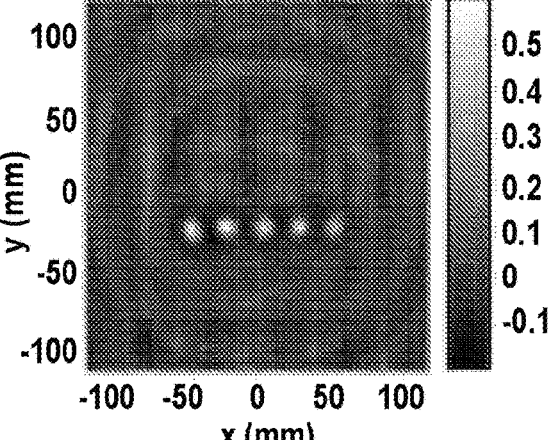
Figures 7A, 7B, 7C:
FIGS. 7A-7C illustrate a comparison of relative x-ray acoustic computed tomography intensity measurements to film in both accuracy and reproducibility, in accordance an example.

In various examples, water tanks, gels, and commercial physical phantoms used in US imaging and training in radiology and radiotherapy can also be used to evaluate XACT dosimetry. Physical phantoms are manufactured geometries with materials that mimic tissue characteristics and simulate realistic irradiation and acoustic imaging conditions. FIGS. 6A-6C uses irradiated physical phantoms to illustrate the sensitivity and dose uncertainties of XACT. FIG. 6A shows a phantom row of 5 lipid (i.e., pork lard) cylinders fixed inside of a porcine gel. Three physical wedges with nominal angles (15°, 30° and 45°) were attached to a 6 MV linac beam using a 10×10-cm field, and the radiation dose was measured in pork lard lipid cylinders using XACT measurements. A single rotating linear element transducer performed the XACT measurements and an EBT3 Gafchromic film acted as a reference. Measurements were repeated 10 times to estimate statistics. FIG. 6B shows an XACT image without a wedge and FIG. 6C shows a 30° wedged XACT image. The normalized measured wedged intensities to normalized no-wedged intensities at middle position are presented in FIGS. 6B and 6C. Estimated uncertainties to resolving the dosage between any two consecutive lard cylinders were found to be between 2-5%, remarkably comparable to those of film (e.g., radiochromic films that are tissue equivalent), with the additional benefit of the 3D and in vivo dosimetric measurement capabilities of XACT. Further, turning to FIGS. 7A-7C which show that XACT measurements with wedge angles demonstrative intensity measurements comparable to film in both accuracy and reproducibility.

FIGS. 8A-8E present a porcine gelatin phantom embedded with both pig fat and muscle tissue. The three rectangles in FIG. 8A indicate the boundaries of radiation fields applied for XACT with the bottom left rectangle outlining a pig fat lipid region, the bottom right rectangle outlining a muscle region, and the top rectangle outlining a background or gelatin region. FIG. 8B presented an US compounding image of the phantom which has reduced speckle noise and shows the phantom morphology clearly. FIGS. 8C-E present XACT images of the phantom with various applied radiation fields which show that XACT can discriminate better between fat and gelatin vs. muscle and gelatin, which is due to varying electron densities that impact Compton interactions at higher radiation energies. The results presented in FIGS. 8A-8E also suggest that different tissues illuminated with the same field (beam shape and energy) differ in radiation dose deposition, which could be beneficially leveraged for patient care by evaluation with XACT-based in vivo dosimetry.

Figure 9D:
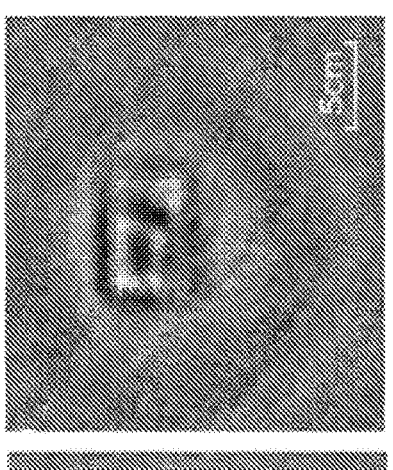
FIGS. 9A-9D display x-ray acoustic computed tomography and ultrasound images of a phantom made of porcine embedded with two pieces of liver, in accordance an example.
Figure 9C:
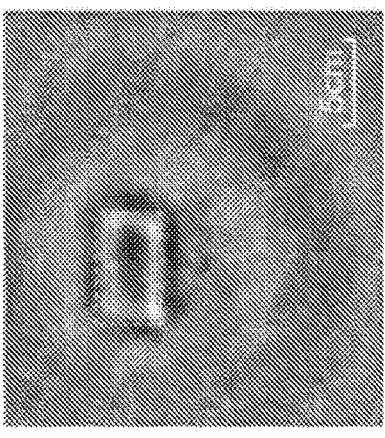
Figure 9B:
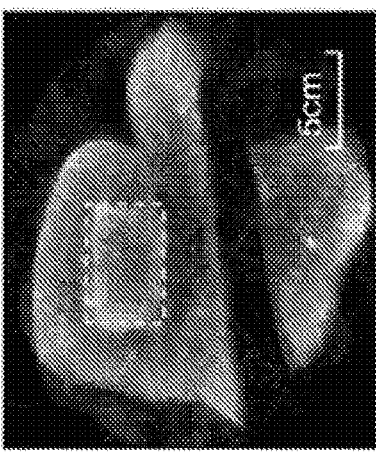
Figure 9A:
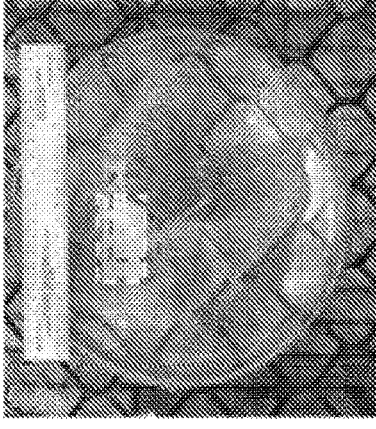

FIGS. 9A-9D present results of measurements on a phantom made of porcine gelatin containing two pieces of liver with a piece of porcine fat embedded into one of the pieces of liver to mimic a liver tumor. FIG. 9A shows a photograph of the phantom, where the two rectangles indicate the boundaries of two radiation fields applied for XACT imaging, to assess misalignment effects due to motion for instance. The upper rectangle covering the tumor indicates the clinical situation of good alignment of a radiation field with the target tumor; while the lower rectangle covers part of the tumor as well as some background gel simulating the clinical situation of bad alignment of a radiation field with the target tumor with a spatially alignment error of less than 3 mm. FIG. 9B is an US compounding image that successfully delineates the morphology of the phantom, including the boundaries of the livers and the tumor, with reduced speckle. FIGS. 9C and 9D are 2D XACT images that show the boundaries of the applied radiation fields. By combining the US and XACT together, the co-registered images can be viewed for both the tissue boundaries, the location of the tumor, the distribution of radiation dose, and the relative position of the radiation field applied onto the sample can be evaluated. The fused US and XACT imaging presented by the demonstrations above are an example of the technologies and methods described herein that may be used to improve the accuracy and efficacy of RT.

As previously stated, XACT provides relative radiation dosage information under different dose rate conditions. Indeed, its performance at ultrahigh delivery is improved due to higher temperature gradients. Conversion of a relative XACT dosage measurement to an absolute XACT dosage measurement requires information the density of tissue and the Grüneisen efficient for that tissue. The Grüneisen coefficient, also called the Grüneisen parameter, is a metric that characterizes how the temperature change of a material changes the volume and dynamics of that material. For example, the Grüneisen coefficient is used to assist in determining how acoustic or electromagnetic waves propagate in a given material, or volume containing multiple materials. The correlation between the relative XACT image intensity, I(r), and the absolute dosage deposited in the tissue, D(r), can be described by:

$$I(r) = K \frac{\Gamma \eta \rho}{\tau} D(r) \qquad (1)$$

where $\Gamma$ is the Grüneisen coefficient, $\eta$ is the thermal efficiency of the tissue, $\rho$ is the density of the tissue, and $\tau$ is the applied dosage radiation pulse duration. The three constants $\Gamma$, $\eta$, and $\rho$ are properties of the tissue in the ROI and can be determined by US or CT measurements of the ROI. The fourth constant in Expression (1), T, is a parameter determined by the RT applied radiation treatment plan. Therefore, the four constants $\Gamma$, $\eta$, $\rho$, and $\tau$ are known values during an RT session that uses a US/XACT system. The factor K is a correction factor is a constant that depends on the specific US/XACT system and the reconstruction algorithm used. The correction factor K may be different for individual US/XACT systems, and the correction factor K can be calibrated through in vitro studies (i.e., submerging materials in tanks of water and imaging tissues in gel phantoms as previously described). The XACT image intensity, I(r), is a measured value and is therefore known during a US/XACT measurement. Therefore, the absolute dose can be calculated by:

$$D(r) = \frac{I(r)\tau}{K\Gamma\eta\rho} \qquad (2)$$

After beam forming is used to spatially map measured relative XACT information, and conversion of the relative XACT data to absolute XACT data is performed, the US imaging of the tissue in a ROI can be fused with the absolute XACT spatial information to determine the amount, and location, of an applied radiation dosage in a ROI. The information may then be displayed, recorded, and/or sent to a processor, controller, or radiation source to adjust the treatment plan for a next radiation dosage.

Figure 10:
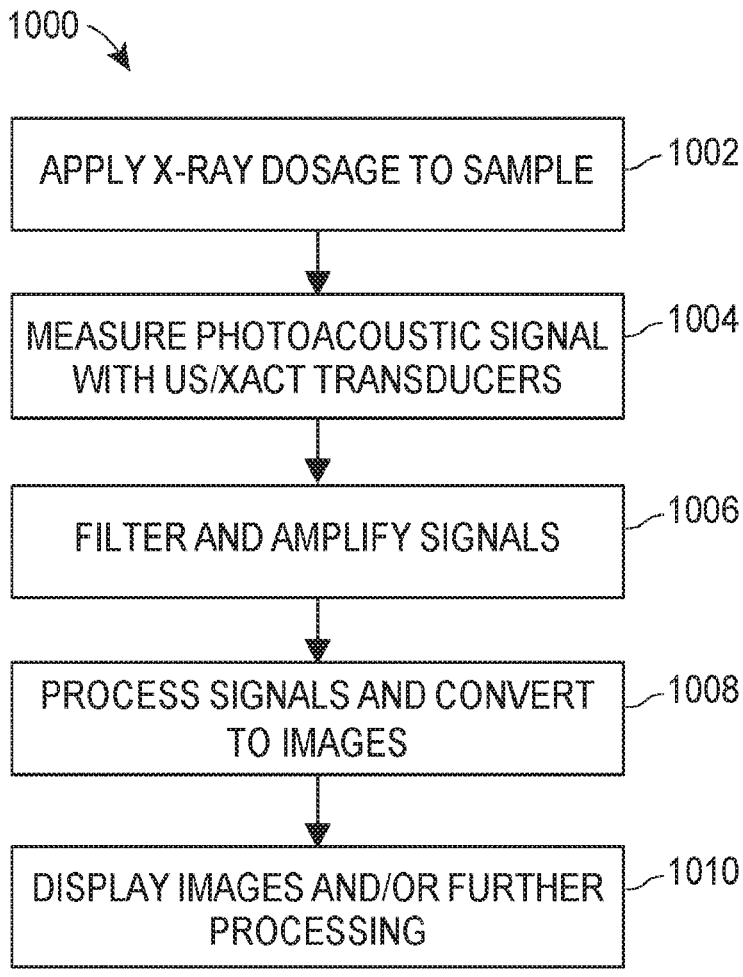
FIG. 10 is a flowchart of an example method for generating images from data acquired during a radiotherapy session with a combined x-ray acoustic ultrasound system, in accordance an example.

FIG. 10 illustrates a method 1000 for obtaining US/XACT images. At a block, 1002 a radiation source, such as source 202 in FIG. 2, applies x-ray radiation to a sample. The sample may be a water tank, gel, body part, or other material in a ROI such as any of the tissues and incongruous regions presented in FIGS. 4A-4C, FIGS. 5A-5D, FIGS. 6A-6C, FIGS. 7A-7C, FIGS. 8A-8E, or FIGS. 9A-9D which contain muscle, lipids, water, metals, and other substances. At a block 1004, a photoacoustic signal is obtained utilizing a US/XACT transducer, such as the transducers 210 of FIG. 2, positioned to obtain US/XACT signals from a sample. The transducers 210 obtaining photoacoustic signals at a block 1004 may be statically positioned or dynamically moving in relation to a target site or ROI.

Figure 12:
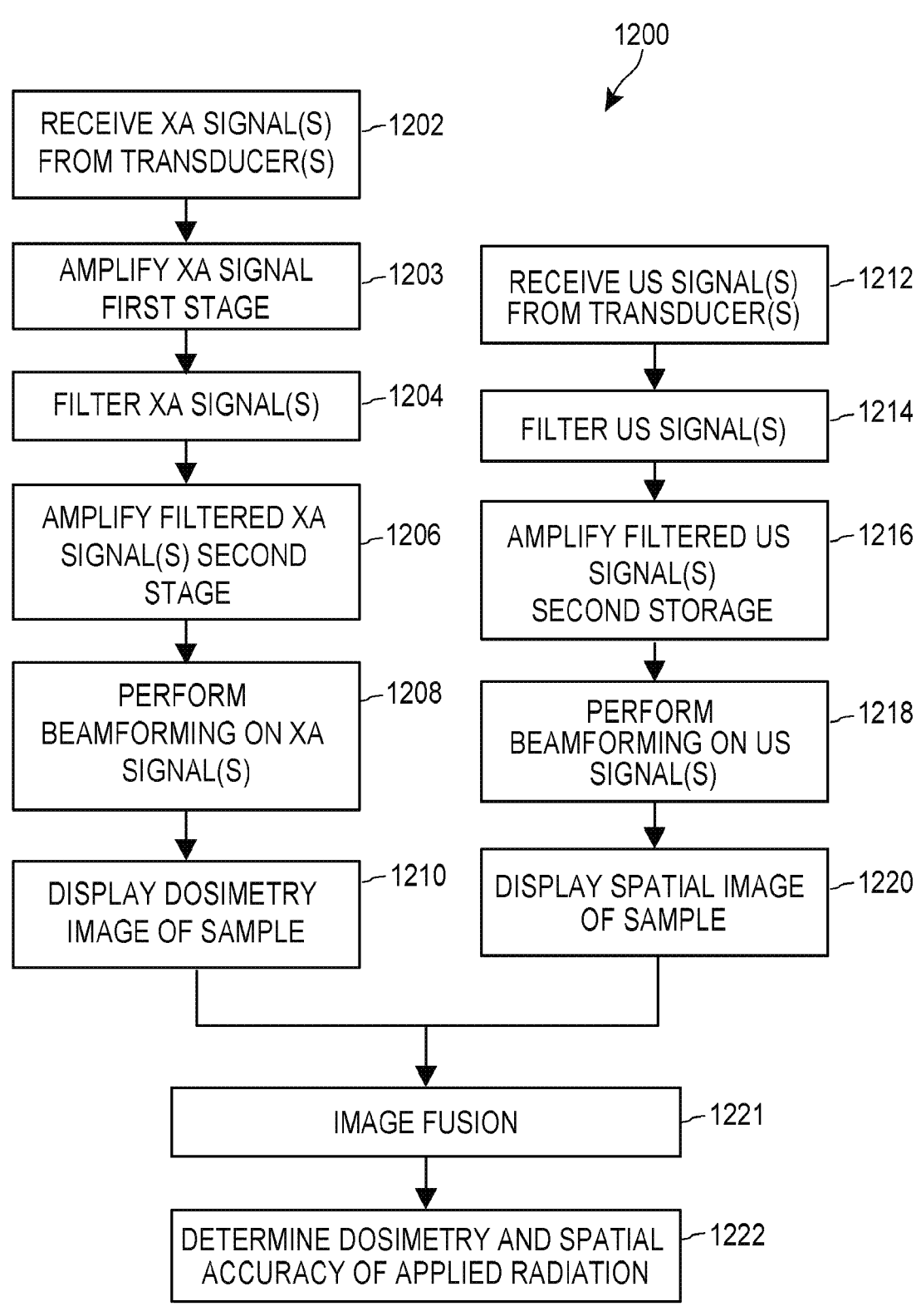
FIG. 12 is a flowchart of an example method for processing x-ray acoustic and ultrasound signals to determine dosimetry and spatial accuracy of a radiation beam during a radiotherapy session, in accordance an example.

At a block 1006, the US/XACT signals may be amplified and/or filtered to increase the electrical signals SNR, reduce noise, and/or isolate certain frequency signals. In embodiments, the transducers may utilizing different transducer elements for XACT and US measurements, as illustrated in FIGS. 3A-3C, and the XACT and US signals may therefore be amplified and filtered independently. Any other electrical manipulation may be made to the XACT and US electrical signals to provide adequate SNR and signal resolution necessary to generate an image of a desired, or required, quality for analysis or feedback control of the applied radiation. FIG. 12 illustrates an example implementation of differentiated amplification and filtering performed on XACT signal and US signal pipelines, respectively.

At a block 1008, the signals may be initially processed by a signal acquisition system, such as the one illustrated in FIG. 2, which collects the electrical signals from the transducers and generates US and XACT images. At a block 1010 the images may then be displayed on a terminal or sent to a processor for further image processing. Further image processing may include 3D reconstruction using data from multiple MAT angles and/or positions, fusing the XACT and US images, or any other image processing technique.

Figure 11:
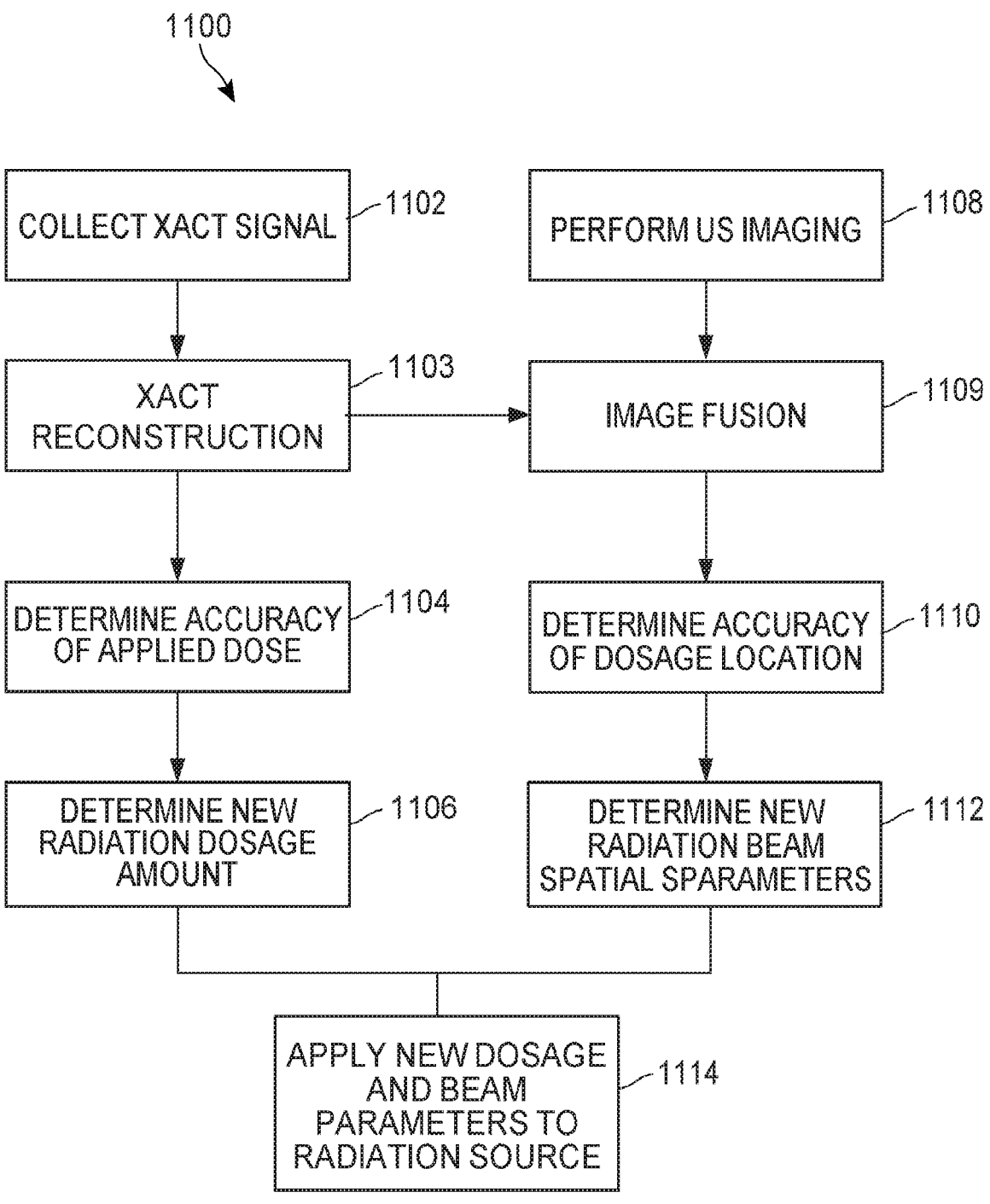
FIG. 11 is a flowchart of an example method for determining the dosimetry and spatial accuracy of applied radiation using a combined x-ray acoustic ultrasound system, in accordance an example.

FIG. 11 is a flowchart illustrating a method that may be implemented for determining the dosimetry and spatial accuracy of applied radiation during radiotherapy. The method 1100 presented in FIG. 11 may be performed using a US/XACT system, such as the system of FIG. 2. At a block 1102, an XACT signal is obtained which may be accomplished using the transducers 210 and signal acquisition unit 212 of FIG. 2. XACT reconstruction which may include beam forming is performed at a block 1103. Discrepancies between the planned and applied dosage are then determined at a block 1104. A new updated dosage intensity is then calculated for the radiation source to reduce discrepancies between the planned and applied radiation dosage at a block 1106.

Anatomical and physiological US imaging is performed at a block 1108 to determine the tumor location, function, and potential changes in the tumor location, potential deformations, or tumor biological status. Image fusion of the relative dosimetry information and the US imaging is then performed at a block 1109. At a block 1110 the planned treatment location is compared to the measured current location of the tumor or ROI to determine the spatial accuracy of the applied radiation dosage. Discrepancies between the planned radiation dosage location and the measured locations of the tumor or ROI are then determined, and new radiation beam spatial parameters are calculated at a block 1112. The updated radiation beam intensity and spatial parameters, determined at blocks 1106 and 1112, are sent to a radiation source, such as the radiation source 202 of FIG. 2, at a block 1114 to improve the accuracy of a next applied radiation dose.

The method 1100 of FIG. 11 is just one embodiment of a method capable of obtaining US/XACT images and determining new radiation beam parameters based off of feedback from the US/XACT imaging system. The method 1100 can be implemented in US/XACT systems to increase the radiation dosage to a tumor or ROI and reduced irradiative contamination to healthy or normal tissues which, among other benefits that can increase tumor treatment efficacy and reduce impairment due to unnecessary tissue toxicity.

FIG. 12 is a flowchart illustrating an example method 1200 for processing XACT and US signals to determine dosimetry and spatial accuracy of a radiation beam during a radiotherapy session. At a block 1202 an x-ray acoustic (XA) induced electrical signal is received from an XACT transducer. The XA signal is amplified by a first stage of amplification at a block 1203, and filtered at a block 1204 to reduce noise, to increase the SNR, and/or to isolate the XA signal frequencies. The filtered XA induced electrical signal is then amplified by a second stage of amplification at a block 1206 to improve signal quality. In embodiments of US/XACT systems, the XA electrical signal may need to be amplified. For example, some signal processing systems, such as the Verasonics system, may need the XACT induced electrical signal to be amplified by 40 dB to generate XACT images of a desired quality. At a block 1208 beamforming is performed, and the dosimetry information is presented as an image on a screen or terminal at a block 1210.

At a block 1212, US induced electrical signals are received from an US transducer. The US induced electrical signals are filtered at a block 1214 to reduce noise, improve the SNR, and/or to isolate the US signal frequencies. At a block 1216 the filtered US induced electrical signals are amplified. For a US/XACT system, such as the system of FIG. 2, implementing a Verasonics device as the signal acquisition system 212, the US induced electrical signal does not need to be amplified. In such cases where a Verasonics system is implemented as the signal acquisition unit, the US induced electrical signal may be fed directly to the Verasonics system, while the XA induced electrical signal must be amplified before being passed to the Verasonics system. Beamforming is then performed on the US signals at a block 1218. The US images of the sample or ROI are then displayed on a screen of terminal at a block 1220. The US images and XACT dosimetry images are then fused at a block 1221. At a block 1222 the XACT and US images may be further processed to determine the applied radiation dosage and spatial accuracy which may be used as feedback information for further beam calibration, as illustrated in FIG. 11.

Figure 13:
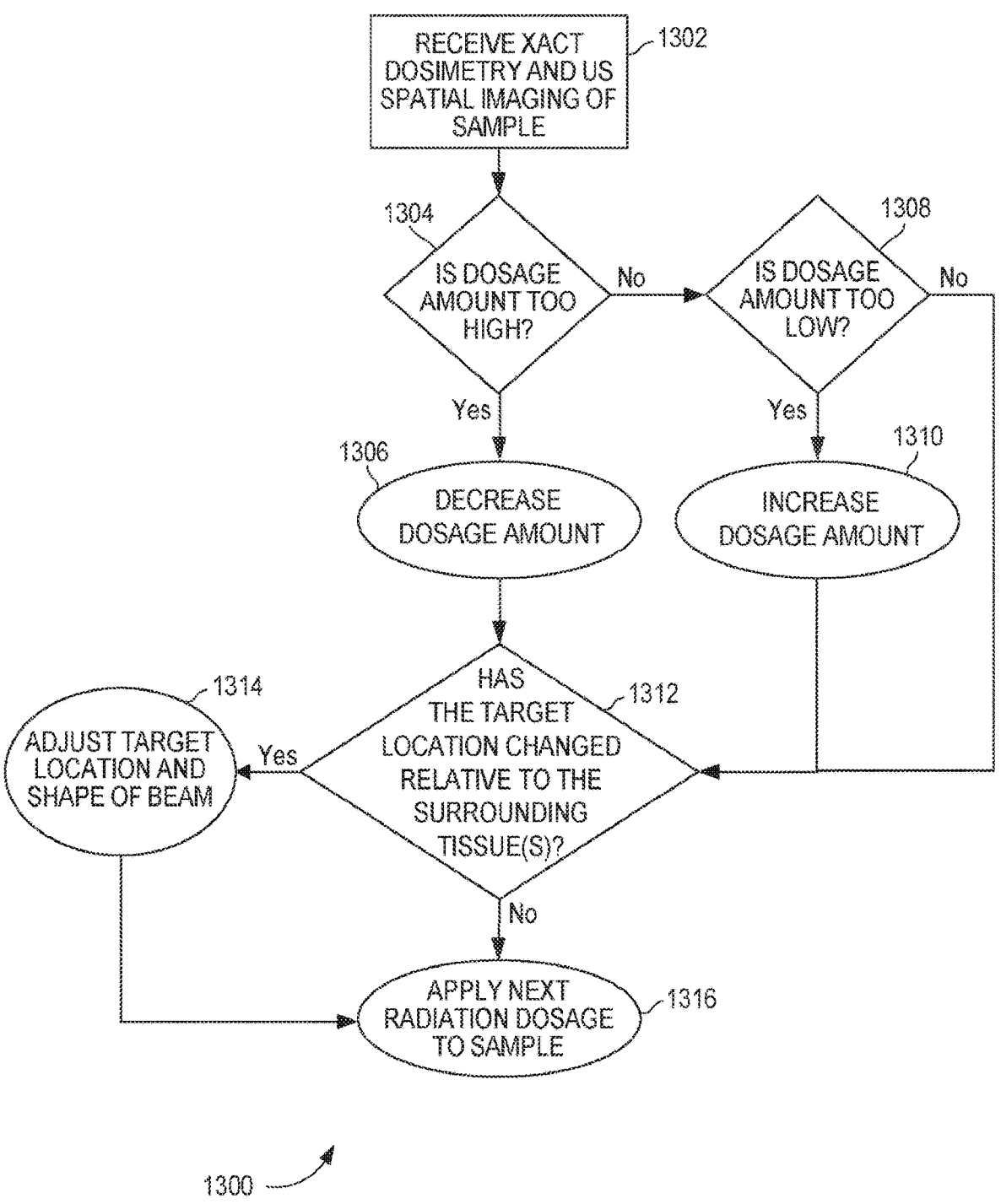
FIG. 13 is a flowchart of an example method for calibrating a next radiation dosage from dosimetry and ultrasound spatial imaging, in accordance an example.

FIG. 13 illustrates a flowchart of an example decision tree method 1300 for determining a next radiation dosage from XACT dosimetry and US spatial imaging. The method 1300 of FIG. 13 may be implemented as a routine in a processor or computer, such as the processor 214 of FIG. 2, configured to alter, process, and/or analyze image data. At a block 1302 XACT dosimetry and US spatial images of a tumor or ROI are received. The image data may be provided by external sources such as the signal acquisition system 212 of FIG. 2, or stored on internal or external memory. Furthermore, the input XACT/US image data may be received via wired or wireless means from any source able to provide data to a processor.

After processing the dosimetry and image data, the dosage amount may be checked, at a block 1304, by determining if the applied dosage amount is higher than a planned dosage amount. If the dosage amount is higher than the planned dosage amount, a new dosage amount is determined by decreasing, at a block 1306, the previously applied dosage amount. If the dosage amount is determined not to be higher than the planned dosage amount, then the dosage amount is checked, at a block 1308, to determine if the applied dosage amount is lower than the planned dosage amount. If the applied dosage amount is lower than the planned dosage amount than a new dosage amount is determined, at a block 1310, by increasing to the previously applied dosage amount. If, at the block 1308, the dosage amount is determined not to be lower than the planned dosage amount then the current dosage amount is neither too high nor too low and is not altered in the current iteration of the method 1300 of FIG. 13. It should be noted than "higher than a/the planned dosage amount" may also be interpreted to be "higher than a/the margin of a planned dosage amount". Similarly, "lower than a/the planned dosage amount" may also be interpreted to be "lower than a/the margin of a planned dosage amount" as a person of ordinary skill in the art would recognize.

At a block 1312 the measured US spatial imaging is compared to the planned treatment. The location of any tumor or ROI, surrounding tissues, organs, the patient's body position, and/or any other observable tissues or factors of interest are compared to the planned or previous dosage configuration. If the geometries and/or locations of any of the tissues or factors of interest have changed or shifted beyond an acceptable range, new spatial beam parameters are determined at a block 1314. A next radiation dosage is applied to the sample or ROI with the updated or maintained dosage amount and spatial beam parameters at a block 1316. If the measured US spatial information matches a planned treatment ROI, or is within a margin of a planned treatment ROI, then no adjusting of the radiation beam location and geometries may be performed required, and a next radiation dosage is applied at a block 1316.

Figure 14:
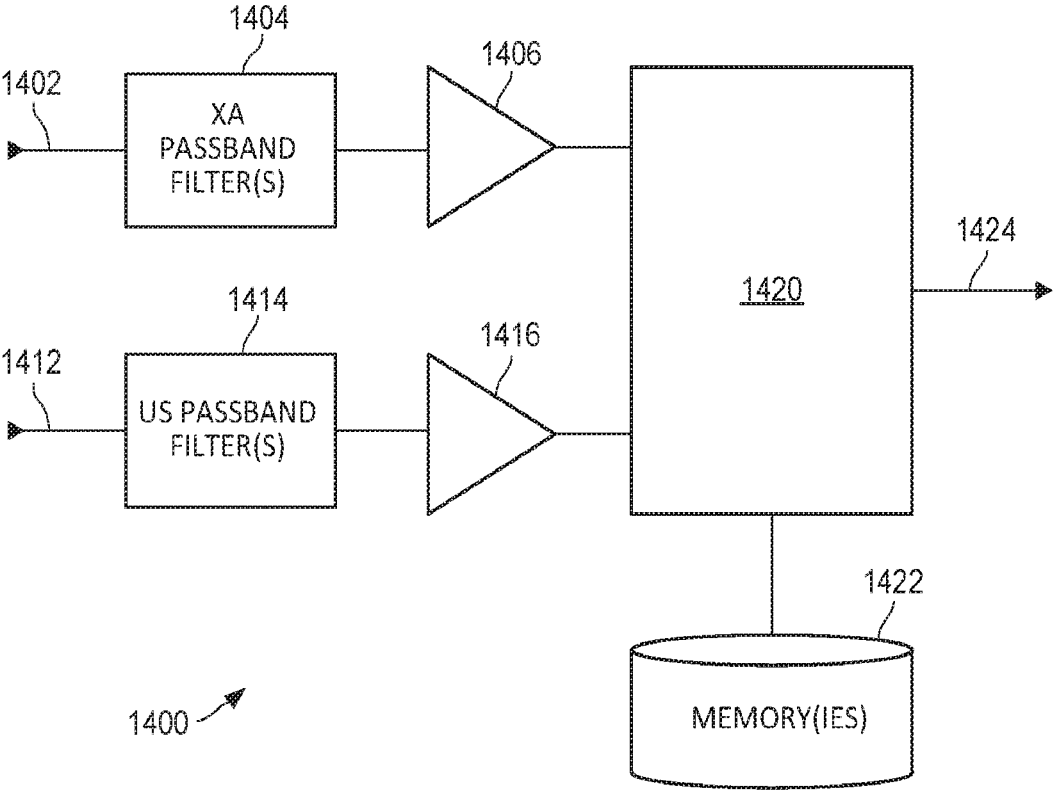
FIG. 14 is a block diagram of an example signal acquisition system for generating images from electrical signals provided by x-ray acoustic and ultrasound transducers, in accordance an example.

FIG. 14 illustrates a block diagram of an embodiment of a signal acquisition system 1400 for generating images from electrical signals provided by transducers. The signal acquisition system 1400 receives XA and US induced electrical signals from an XA transducer on an electrical communication channel 1402. A band-pass filter 1404 filters out electrical signals with frequencies outside of the XA frequency band to isolate the XA signal and reduce out-of-band noise. An amplifier 1406 amplifies the XA electrical signal, and a processor 1420 performs further processing and manipulation of the data to generate images.

The signal acquisition system 1400 receives the US induced electrical signal from an US transducer on an electrical communication channel 1412. A band-pass filter 1414 filters out frequencies outside of the US frequency band to isolate the US signal and reduce out-of-band noise. An amplifier 1416 amplifies the US electrical signal, or, as discussed above, in embodiments employing a Verasonics system as the signal collection system 212 of FIG. 2, no amplification of the US electrical signal is necessary. A processor 1420 receives the US induced electrical signal to do further processing and manipulation of the data to generate images.

The processor 1420 carries out routines to generate images from the US/XACT input data. The dosimetry and tissue images may be displayed independently or the XACT/US information may be comingled and displayed in a single image. The images be sent to another processor, by an output terminal 1424, for further analysis. The output terminal 1424 may be connected to an external wired or wireless network, to a display or terminal, to a printer, to one or more memories, or to any other device or medium for further use. The processor 1420 may also send the image data to one or more memories 1422 that store the image data. The one or more memories 1422 may be volatile memory or non-volatile memory and may each include one or more non-transitory, tangible, computer readable storage media such as random access memory (RAM), read only memory (ROM), FLASH memory, a biological memory a hard disk drive, a digital versatile disk (DVD) drive, etc.

In an embodiment, the one or more memories 1422 may store instructions or routines executable by processor 1420 or central processing unit (CPU). The instructions stored on the one or more memories 1422 may include instructions for beam formation, patching images from multiple transducers together, creating 3D images from multiple images, patching images together from a single transducer at different angles or positions (e.g., a single rotating around a ROI), the routines may be configured to further filter, amplify, multiplex, sharpen, apply spatial correction, or may be any other routine required to form dosimetry and spatial images from the input XA and US electrical signals. The routines need not be implemented as separate software programs, procedures, or modules, and thus various subsets of the routines can be combined or otherwise re-arranged in various embodiments. In some embodiments, at least one of the memories 1422 stores a subset of the routines and data structures identified herein. In other embodiments, at least one of the memories 1422 stores additional routines and instructions not described herein.

The signal acquisition system 1400 of FIG. 14 is only one example of a signal acquisition system for XACT/US imaging. Other embodiments of signal acquisition systems may have more or fewer components than shown in FIG. 14, have one or more combined components, or have a different configuration or arrangement of the components. Moreover, the various components shown in FIG. 14, may be implemented by hardware, by a processor executing software instructions, or by a combination of both hardware and a processor executing software instructions, including one or more signal processing and/or application specific integrated circuits.

Figure 15:
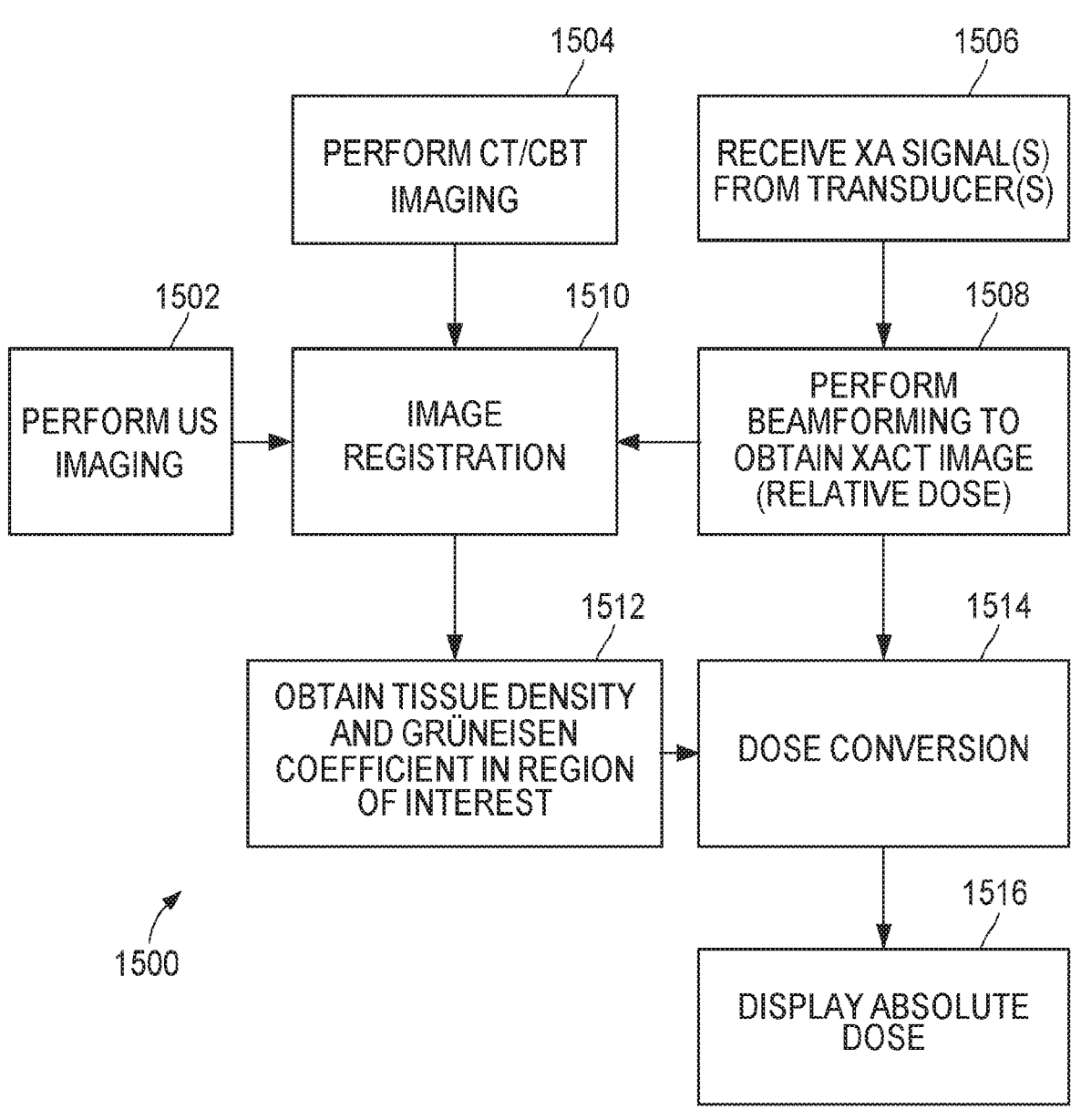
FIG. 15 is a flowchart of an example method for obtaining absolute dosimetry using combined x-ray acoustic dosimetry and ultrasound imaging, in accordance an example.

FIG. 15 is a flowchart of an example method for obtaining absolute dosimetry information using combined XACT dosimetry and US imaging. At a block 1502 US imaging is performed on a ROI, and alternatively or simultaneously a CT or conebeam CT (CBCT) scan may also be performed on a ROI at a block 1504. At a block 1506 an XA signal is received from XA transducers. Beamforming on the received XA signals is performed at a block 1508 to obtain relative XACT image dosimetry of the ROI. Image registration of the US image, CT/CBT image, and relative XACT dosimetry image is performed at a block 1510. The image registration may include fusion of images from the various measurements such as fusion of the US and XACT images to identify the amount of applied radiation received by various regions and tissues in the ROI. The tissue density and Grüneisen coefficient is then determined from the US and CT/CBT images at a block 1512. The relative XACT dosimetry information may then be converted to absolute dosimetry information using the tissue density and Grüneisen coefficient at a block 1514. The absolute radiation dosage map for a ROI may then be displayed at a block 1516. The absolute dosimetry information may then be used to calibrate the intensity of a next applied radiation dose, and the spatial information may be used to alter the radiation deliver site and beam geometries of a next applied radiation. The analysis and conversion from relative to absolute dosimetry information may be performed in a processor such as the processor 214 of FIG. 2. The processor may then provide new radiation dose beam intensities and beam geometries to a radiation source 202 through a communicative connection 216.

As previously described, the disclosed system and methods may be implemented in ultra-high dose (>40 Gy/s) radiotherapy, such as FLASH-RT. It has been demonstrated in mice that irradiation under FLASH-RT conditions has reduced deleterious neurocognitive effects, such as deficits in learning and memory, compared with mice treated with conventional RT. Additionally, studies with mice have also shown a significant reduction in lung fibrosis under FLASH-RT. Furthermore, the benefits of FLASH have been seen in higher mammals including trails showing minimal side-effects in humans. As previously mentioned, dosimetry using FLASH-RT is limited to surface measurements due to a number of detector Inefficiencies and other factors. In conventional RT a clinical linac delivers a small radiation dose (~0.5 mGy) in a series of pulses which is small compared to the dose typically used in treatment. The small dose pulses allow the mean dose rate to be measured by averaging the dose over seconds or minutes. Due to the high dose per pulse applied during FLASH-RT, only a few pulses (e.g., less than ten, or on the order of tens of pulses) would be used for each treatment, thus averaging pulses is not viable and dose measurements on a pulse-to-pulse basis are essential.

As previously mentioned, many commonly implemented dosimetry methods are not feasible for FLASH-RT due to the high dosage rates of FLASH-RT (e.g., ionization chambers). Film may be implemented in FLASH-RT dosimetry, as film may be dose rate independent and can be placed directly on the surface of the patient. However, film is not a real-time measurement, which is better suited for quality assurance of the treatment plan rather than in vivo measurements and may not be useful for treatment calibration. Other dosimetry methods may be used for FLASH-RT, but they are typically limited to surface measurements and do not allow for any real time feedback, dose measurements in deep tissue, or for the measurement of the treatment volume for each linac pulse. The disclosed system and methods enable the registration and mapping of a dose with a patient's anatomy to ensure that the radiation is applied and deposited accurately and safely at the intended target in real-time, which is not possible with current clinical dosimetric techniques for conventional or FLASH-RT. The disclosed system and methods overcome the drawbacks of current dosimetric and applied radiation monitoring techniques by combining both US and iRAI information to determine a dosage amount and region of an applied dosage for conventional and FLASH-RT. In embodiments described herein, the US and iRAI measurements may be performed simultaneously to directly map dosimetry and anatomical information and further to provide feedback to a radiation source for the application of a future or next dose. Alternatively, the US and iRAI measurements may be performed at different times as required or desired for therapeutic purposes, or for compensating for signal delays and/or other environmental and biological factors. In embodiments, multiple US and iRAI measurements may be performed to generate multiple image frames for analyzing dosimetry and anatomical information and/or for creating real-time videos and imagery of dosimetry and anatomical information for region of interest.

A radiation generated pressure wave is directly proportional to the tissue specific Grüneisen parameter and the rate of change of deposited radiation dose. In the case of conventional RT, the rate of change of the deposited dose is on the order of 0.05 cGy per pulse, which requires a high gain pre-amplification stage and substantial pulse averaging. For FLASH-RT, the dose per pulse is on the order of 20 cGy, which is with the range for a typical transducer to detect a pulse and to generate a signal well above the noise level. The implementation of the system and methods disclosed within a FLASH-RT framework enables single-pulse real time dosimetry for ultra-high dose RT.

Typically, in conventional RT, the dose rate that is reported is the average dose rate, $D_r$, which is the dose deposited over a specified time frame (i.e., Gy/min or Gy/s). Additionally, the dose rate can be defined as the rate at which the dose is deposited over a single linac pulse, this is known as the instantaneous dose rate, $'D_p$ (Gy/s). FLASH-RT implements a pulsed delivery system, such as a linac, and it is therefore useful to consider the amount of dose that is deposited from a single pulse, $D_p$ (Gy/pulse) since the full prescribed dose can be delivered over a small number of pulses (e.g., less than ten or on the order of tens of pulses). In the examples that follow, iRAI signal amplitudes are compared to the delivered dose per pulse $D_p$.

Figure 16:
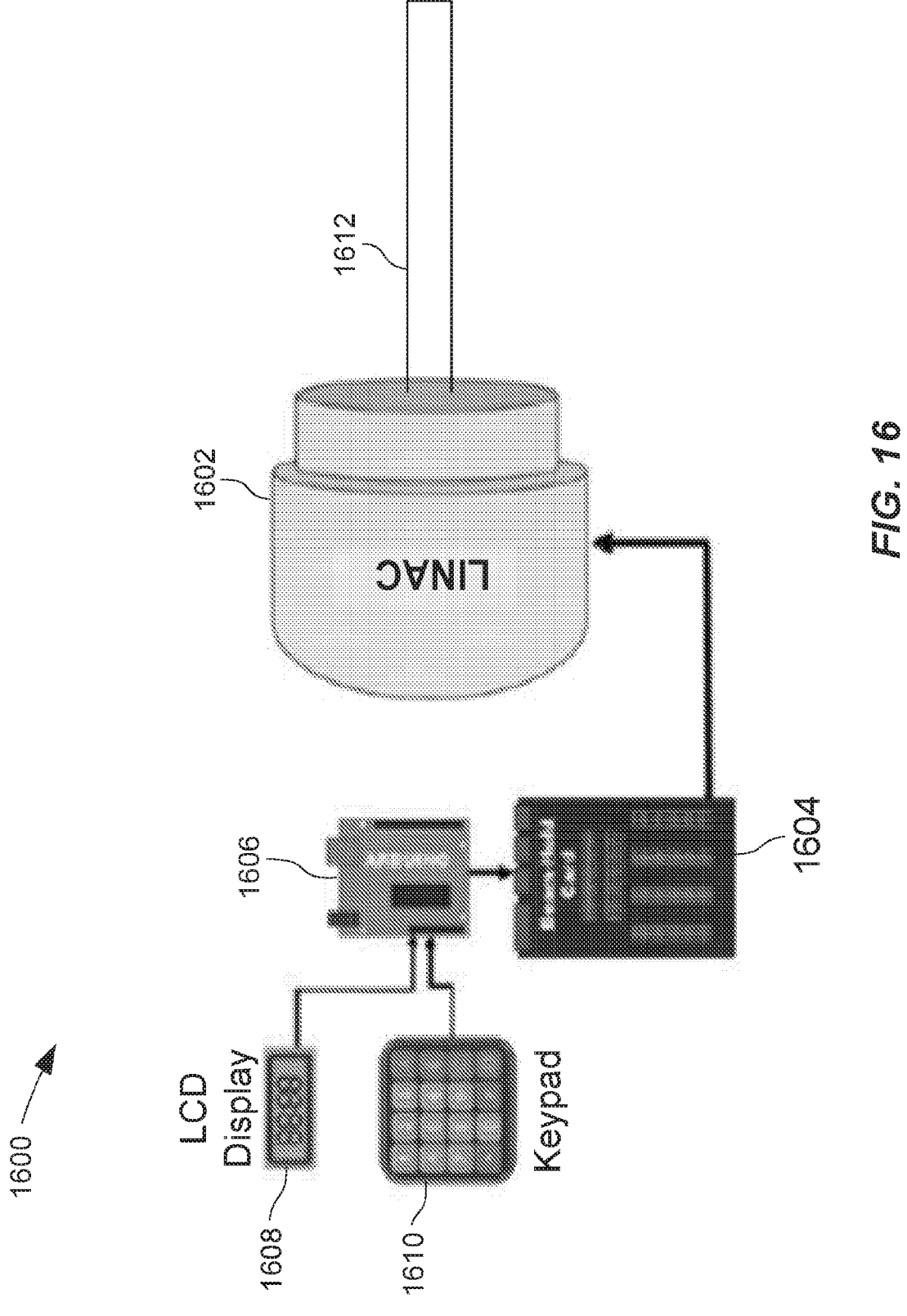
FIG. 16 is a schematic diagram of an Arduino-based linac monitoring and control system, in accordance with an example.

FIG. 16 is a schematic of an Arduino-based linac monitoring and control system 1600 connected to a linac beam-hold card 1604 to control the time that a linac beam 1612 is turned on. The system 1600 includes a linac 1602, a beam-hold card 1604, and an Arduino 1606. Additionally, the system 1600 includes input/output devices such as an LCD display 1608 and a keypad 1610. For the following examples, a Varian Clinac 2100EX (Varian Medical Systems, Palo Alto, Ca) linear accelerator was used as the linac 1602 to assess iRAI for real-time dosimetric imaging with electron beams at FLASH-RT level dose rates (e.g., >40 Gy/s). The linac 1602 was operated in 6 MV photon mode, which, typically, has the highest electron current compared with other modes, with the target and the flattening filter removed. The target was made to retract in 6MV mode by reversing the wiring to the gantry air manifold, which activated the solenoids for positioning the target for low energy X-ray mode vs electron mode. The electron current at the target was measured through a "Target" BNC connector on the control panel to be 100 mA before the target was removed. A monitor chamber functioned as a scattering foil for spreading out the electron beam 1612. The configuration for the following example allows for FLASH dose rates at the linac gantry isocenter for the 100 cm source-axis distance (SAD) linac, illustrated in FIG. 17). The presently discussed configuration focused on linac modifications where the linac 1602 was running in electron mode (i.e., smaller electron current) and measurements took place within the linac head. The system design and method for the following example removed the constraint of limited space within the linac head, allowing for flexibility in experimental designs for iRAI.

The electron beam 1612 was controlled using the Arduino 1606. The Arduino 1606 was an Arduino Uno microcontroller that was connected to the beam hold card 1604. The beam 1612 was able to be turned on for as low as approximately 1 ms at a time, therefore providing single pulses every 1 ms. In embodiments, the pulse duration and repetition rate may be determined by the radiation source (e.g., linear accelerator). The electron pulse had a duration of 4 μs and repetition rate of 330 HZ. The beam run time was entered using the keypad 1610, displayed on the LCD display 1608, and communicated to the Arduino 1606. During beam delivery with service mode, the beam 1612 would be turned on and the Arduino 1606 would maintain this beam hold until the trigger, releasing the beam 1612 for the desired time.

Radiation dose was measured using GAFChromic EBT-XD dosimetry film (Ashland Advanced Materials) which was scanned using an Expression 10000XL (Epson) flatbed scanner at a resolution of 72 dpi. All film was analyzed using the FilmQA Pro 2016 software (Ashland Advanced Materials) with the dose map being generated using the built-in triple channel uniformity optimization. Dose was determined from an average of a 0.2 cm×0.2 cm region of interest at the central axis of the beam 1612. Calibration was done using a 10 cm×10 cm field of 6MV photons at reference conditions, where the film is placed at 100 cm SAD with 10 cm of Solid Water (Sun Nuclear Corporation) placed on top with a calibration range of 0 to 50.51 Gy. The dose per pulse was determined by dividing the measured dose from film during a specified timeframe by the known number of pulses acquired during the same period.

Figure 17:
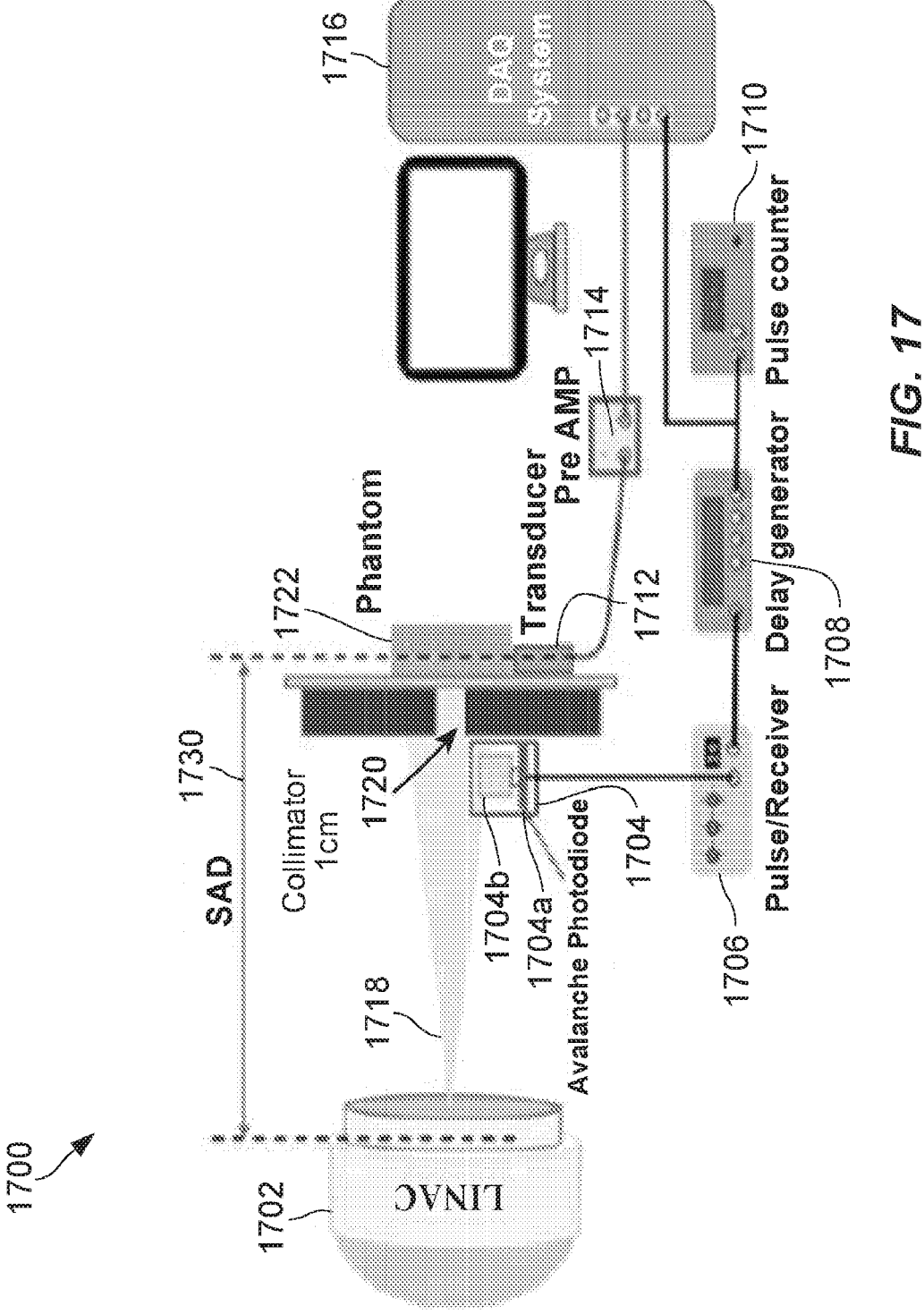
FIG. 17 is a schematic diagram of a system for performing iRAI dosimetric measurements, in accordance with an example.

For the following examples, individual linac pulses were used as acquisition trigger signals for iRAI. FIG. 17 is a schematic diagram of a system 1700 for performing iRAI dosimetric measurements. The system 1700 includes a linac 1702 (i.e., the linac 1602 of FIG. 16), an avalanche photo-diode (APD) 1704*a*, a pulse/receiver 1706, a delay generator 1708, and a pulse counter 1710. The system 1700 further includes a transducer 1712, pre-amp 1714, and a DAQ system 1716, which together perform the iRAI portion of the system 1700. Individual linac pulses were used as acquisition trigger signals for performing iRAI. The APD 1704*a* was a silicon APD (ThorLabs APD101A). The APD 1704*a* measured the Cerenkov Emission (CE) generated in a water/glycerin solution 1704*b* during each single pulse. A container 1704 held the solution 1704*b* and the APD 1704*a*. The container 1704*b* was wrapped in light-blocking masking tape (ThorLabs, T743) to prevent photodetector saturation due to ambient lights. The APD 1704*a* and solution 1704*b* were placed before the electron beam 1718 was collimated and was out of the central axis of the beam 1718, relying off scattered electrons to generate the CE during the time period when the beam 1718 was ON. The signal from the APD 1704*a* was carried over a 15 m BNC cable (50 ohm), was amplified (Olympus, 5072PR) and sent to the delay generator 1708 (Stanford Research Systems, DG535) to generate a square pulse, which then was sent through a splitter. One signal was sent out of the splitter to the analogue pulse counter 1710 (Tennelec, TC 532) and the other signal was sent out of the splitter to the trigger input of the DAQ 1716 of the iRAI portion, as shown in the schematic in FIG. 17.

The dose per pulse was varied and compared with the resultant iRAI signal amplitude to determine the linearity of the iRAI signal amplitude with the dose delivered for each FLASH linac pulse. The electron beam is divergent and therefore the dose per pulse was changed by varying the distance between the beam source, defined where a linac bremsstrahlung target would be placed and the transducer scanning plane, which is referred to as the source-axis distance (SAD) 1730. The SAD 1730 had a range of 100-210 cm with a step size of 10 cm. The dose sensitivity and accuracy were further evaluated by adjusting the SAD 1730 from 102 cm to 104 cm with a finer increment size of 0.5 cm. At each SAD 1730 position, the iRAI acoustic signal was measured and the measurement was repeated 30 times for further statistical analysis.

A collimator 1720 made from water equivalent plastic (Solid Water, Gammex) was placed in front of a cylindrical phantom 1722 to shape the incident electron beam 1718 down to a 1 cm×1 cm square. The phantom 1722 had a diameter of 100 mm and was made of porcine gelatin (10 g/100 ml, G2500, Sigma-Aldrich). Then the beam 1718 was on, the phantom 1722 was used to generate the iRAI signals. The ultrasound transducer 1712 was a cylindrically focused immersion transducer (12550 1001, Imasonic) with a central frequency of 0.5 MHz and a 6 dB bandwidth of 60%. The transducer 1712 was placed on the cylindrical surface of the phantom 1722 and the transducer 1712 and the phantom 1722 were physically coupled with ultrasound gel.

During times when the beam 1718 was on, an iRAI acoustical wave was generated from the irradiated area within the phantom 1722, and the wave propagated through the phantom 1722. The transducer 1712 then detected the wave. The detected iRAI signal was amplified by a pream-plifier 1714 (5660B, Olympus-NDT) with a 40 dB gain before going to the DAQ 1716. The DAQ 1716 included a 14-bit digitizer card (Razor 14, GaGe) with a sampling rate of 10 MHz. The DAQ 1716 was triggered using the linac pulse monitoring system 1600 of FIG. 16.

Film was used as a standard dosimetric device to correlate iRAI signal amplitudes with the dose per pulse, $D_p$. At the same SAD 1730 positions as the iRAI measurements, film measurements were performed with 150 ms of electron beam illumination by controlling the beam 1718 using the Arduino. An analogue pulse counter counted the number of linac pulses. The film was placed in between two pieces of solid water. The piece of solid water facing the collimator 1720 was 1 cm thick, for dose build-up, and the other piece of solid water facing away from the collimator 1720 was 2 cm thick, for backscatter and mechanical support. The results of the measurements performed with the system 1700 of FIG. 17 will be discussed further with respect to the plots of FIGS. 20A, 20B, ands 21.

Figure 18:
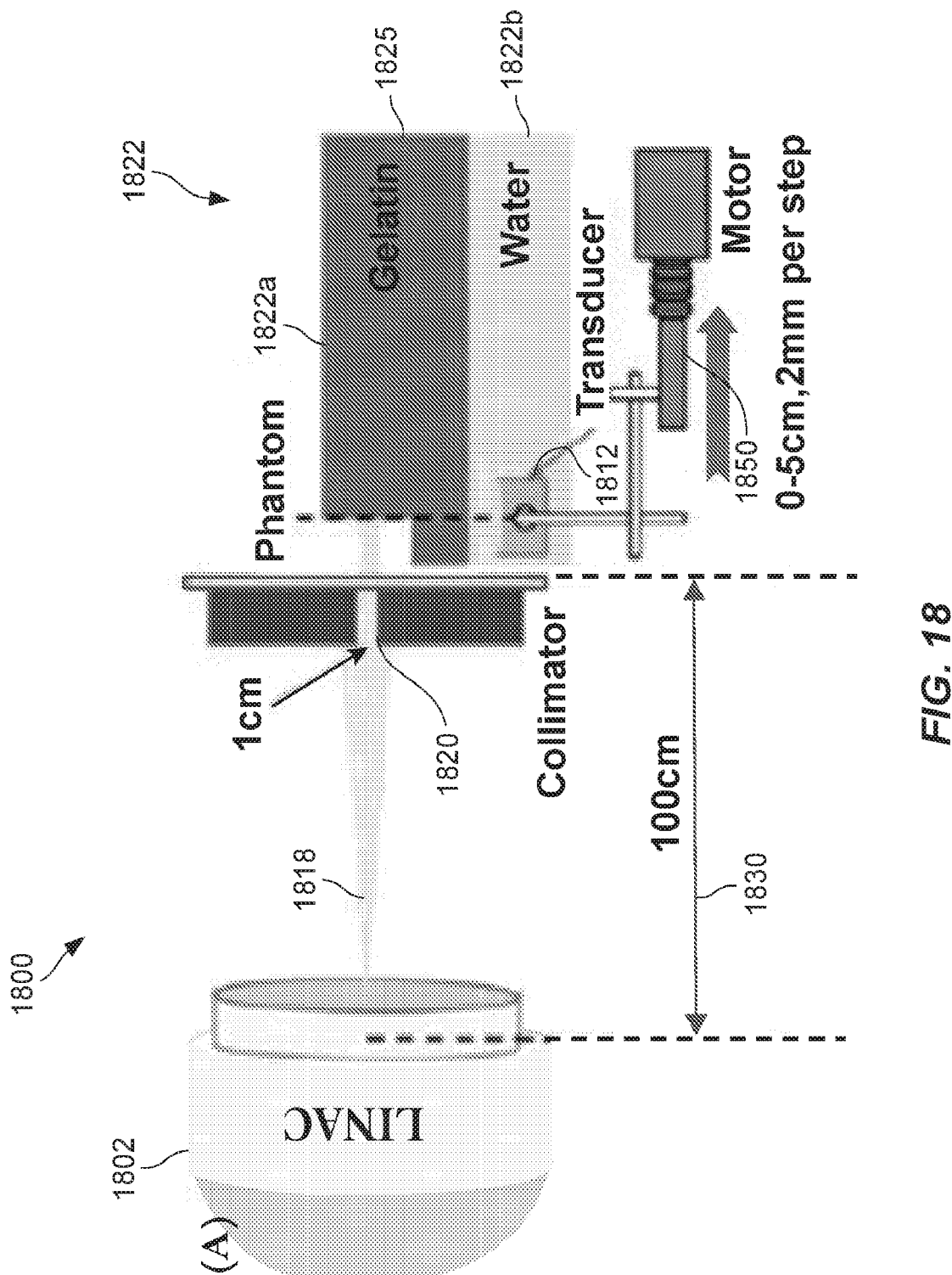
FIG. 18 is a schematic diagram of a system for measuring acoustic depth dose measurements, in accordance with an example.

A typical measurement in clinical quality assurance is the depth dose curve where dose is measured as a function of depth. Depth dose measurements are typically performed using an ionization chamber in a water tank. To assess the feasibility of using iRAI to measure dose at depth, a single element transducer was used to sample iRAI signals at various depths. Additionally, for comparison, the depth dose was also measured using a film at various depths in water. The film was chosen over using an ionization chamber due to recombination saturation during the ultra-high dose rates of FLASH-RT. FIG. 18 is a schematic diagram of a system 1800 for measuring the acoustic depth dose measurement. The system 1800 includes a special phantom 1822 consisting of porcine gelatin 1822*a* and water 1822*b* fixed in a water tank 1825. The special phantom 1822 was used to measure how the deposited dose changes with tissue depth, defined as a percentage depth dose [PDD] curve, during FLASH-RT. A transducer 1812 was immersed in the water 1822*b* on one side of the tank 1825 for acoustic coupling during the scanning process. The porcine gelatin 1825 had 10 cm removed from the front to get a sharp front edge while also allowing the center of the transducer 1812 to be aligned with this front edge of the gelatin 1825. The wall of the water tank 1825 along the beam path was removed to minimize any additional scattering of the electron beam 1818. The solid water pieces (1 cm×1 cm) were placed at the surface of the water tank 1825 facing the collimator 1820 and the collimated electron beam traveled through 10 cm of air before hitting the front edge of the phantom 1822. The initial position of the transducer 1812 was where the center of the transducer 1812 focal plane aligned with the front edge of the porcine gelatin 1822*a* of the phantom 1822. The distance between the center of the electron beam 1818 and the detection surface of the transducer 1812 was 1.12 cm, which is the focal length of the focused transducer 1812. The transducer 1812 was fixed to a motorized translation stage 1850 using optical rods (Low-Profile Motorized Translation Stage, MTS50-Z8, Thorlabs) to allow the focus of the transducer 1812 to be scanned along the electron beam path through the phantom 1822 for a distance of 50 mm with a step size of 2 mm. The iRAI acoustic signal was measured 30 times at each position for statistical evaluation. Film measurements were setup using a custom 3D printed Gafchromic film holder with the distance of 2 mm between each piece of film. The first position of the film was on the surface of the custom holder, which was aligned to be the distance as the front edge of the porcine gelatin 1822*a* of the phantom 1822. The gaps between each adjacent films were filled with water to achieve similar radiation attenuation as the porcine gel 1822*a*. To accumulate a sufficient dose for film analysis, 500 ms (150 pulses) of irradiation time was used. The results of the acoustic depth dose measurements performed with the system 1800 of FIG. 18 are further discussed in reference to the plots of FIG. 22.

Figure 19:
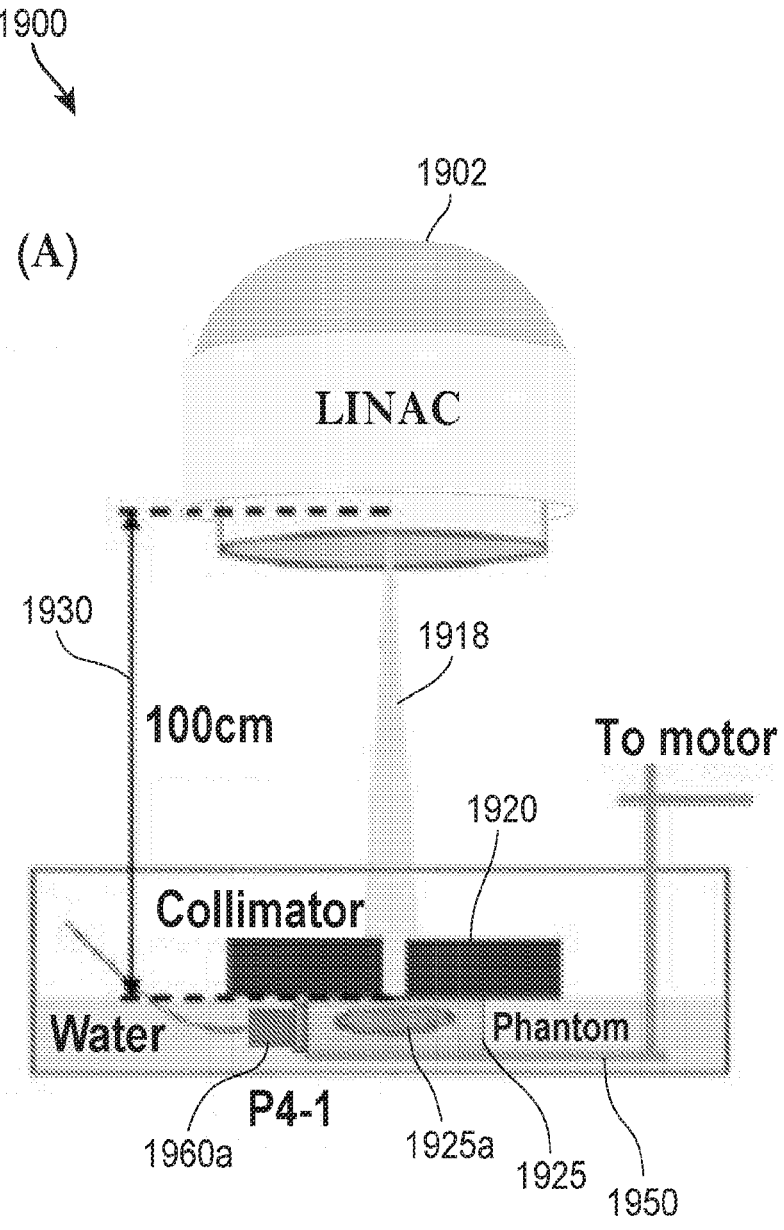
FIG. 19 is a schematic diagram of a system for real-time dual modality dose mapping of a rabbit liver, in accordance with an example.

FIG. 19 is a schematic of a system 1900 for real-time dual modality dose mapping. A cylindrical porcine gelatin phantom 1925 (diameter=100 mm) with a whole rabbit liver 1925a embedded inside was used to evaluate the feasibility of real-time single pulse dose mapping with respect to soft tissue anatomy. A clinically-ready integrated dual-modality imaging system adapted from a commercially available research US platform (Verasonics, Vantage 256) was used to perform both iRAI and B-mode US imaging. The US platform had 256 parallel channels, the platform drove two phased array probes 1960a and 1960b. The first probe 1960a illustrated in FIG. 19 is oriented along the height, or long axis of the cylindrical phantom 1925, and the second probe 1960b (not pictured) was oriented orthogonally to the first probe 1960a along a radial axis of the cylinder (Philips P4-1, 1-4 MHz, 96 elements) simultaneously. The two probes 1960a and 1960b were positioned to face the center of the gelatin phantom 1925 aimed at the rabbit liver 1925a sample A linac 1902 provided radiation to the rabbit liver 1925a from the with a solid water collimator 1920 above the phantom to shape the beam 1918 to a 1 cm×1 cm square. The probes 1960a and 1960b scan planes were a 100 cm SAD 1930 where a dose rate of 25 cGy per pulse was achieved. Both of the probes 1960a and 1960b and the phantom 1925 were immersed in water for ultrasound coupling. The phantom 1925 was driven by a motorized stage 1950 (Low-Profile Motorized Translation Stage, MTS50-Z8, Thorlabs) moving at a velocity of 3 mm/s in the direction along the long axis of the cylindrical phantom 1925 to mimic organ motion. The sample moved a total distance of 50 mm over a time period of 16.7 s. The results of the dual modality dose mapping performed by the system 1900 of FIG. 19 are further discussed in reference to FIGS. 23A-23E.

As in the system 1700 of FIG. 17, each of the systems 1800 and 1900 of FIGS. 18 and 19 also provided signals to a pulse receiver 1706, delay generator 1708, pulse counter 1710, DAWQ, 1716, and pre-amp 1714, and/or other electronics for performing iRAI measurements. Additionally, the linac radiation sources 1702, 1802, and 1902 of FIGS. 17, 18, and 19 were controlled by linac pulse monitoring systems such as the system illustrated in FIG. 16. The triggers from the delay generator of the linac pulse monitoring system 1600 of FIG. 16 were sent to a dual-modality imaging system, such as the Verisonics systems described herein, for synchronization. The iRAI signals from each linac pulse were acquired by the imaging system with iRAI images reconstructed and displayed in real time. For US B-mode, probes were driven by the Verasonics system which displayed the B-mode images.

Figures 20A, 20B:
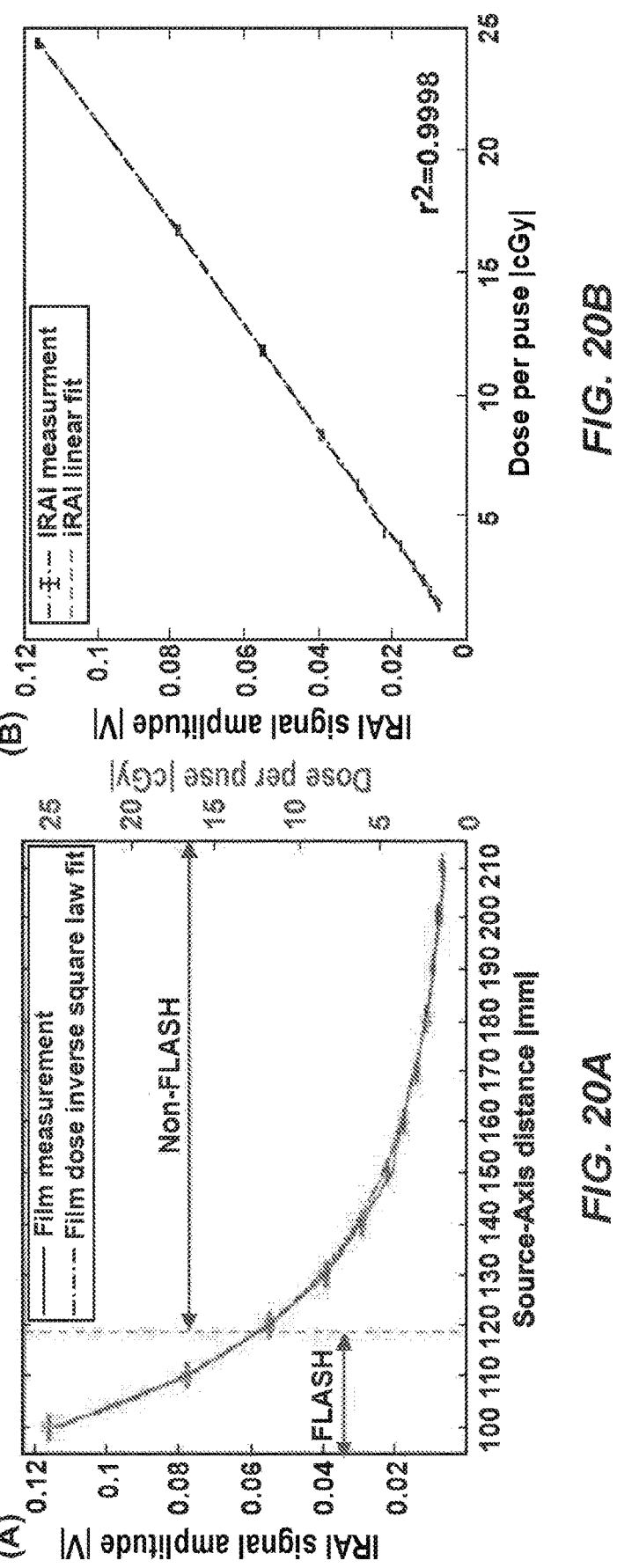
FIG. 20A is a plot of the iRAI dose measurement compared to film measurement at different SAD, in accordance with an example.
FIG. 20B is a plot of the linearity of the iRAI dosimetric measurement against dose per pulse, in accordance with an example.

FIGS. 20A and 20B are plots comparing iRAI dose measurements and film measurement performed by the system 1700 of FIG. 17. FIG. 20A plots the iRAI dose measurement compared to film measurement at different SAD. The boxplot consists of 30 measurements at each SAD, demonstrating the high stability of iRAI for dosimetric measurements. The film measurements show that the dose per pulse decreases with increasing SAD, ranging from 24.5 cGy/pulse at 100 cm SAD to 1.4 cGy/pulse at 210 cm SAD. The iRAI amplitude measurements followed the same decreasing trend with an RSME value of 0.00073. FIG. 20B plots the linearity of the iRAI dosimetric measurement against dose per pulse. A linear relationship is found with an r2 value of 0.9998 between the iRAI signal amplitude versus the film measured dose per pulse, demonstrating high linearity for iRAI dosimetric measurements, and thus demonstrating the feasibility of iRAI for use in dosimetry. The fitting line has proportionality factor of 0.0047.

Figure 21:
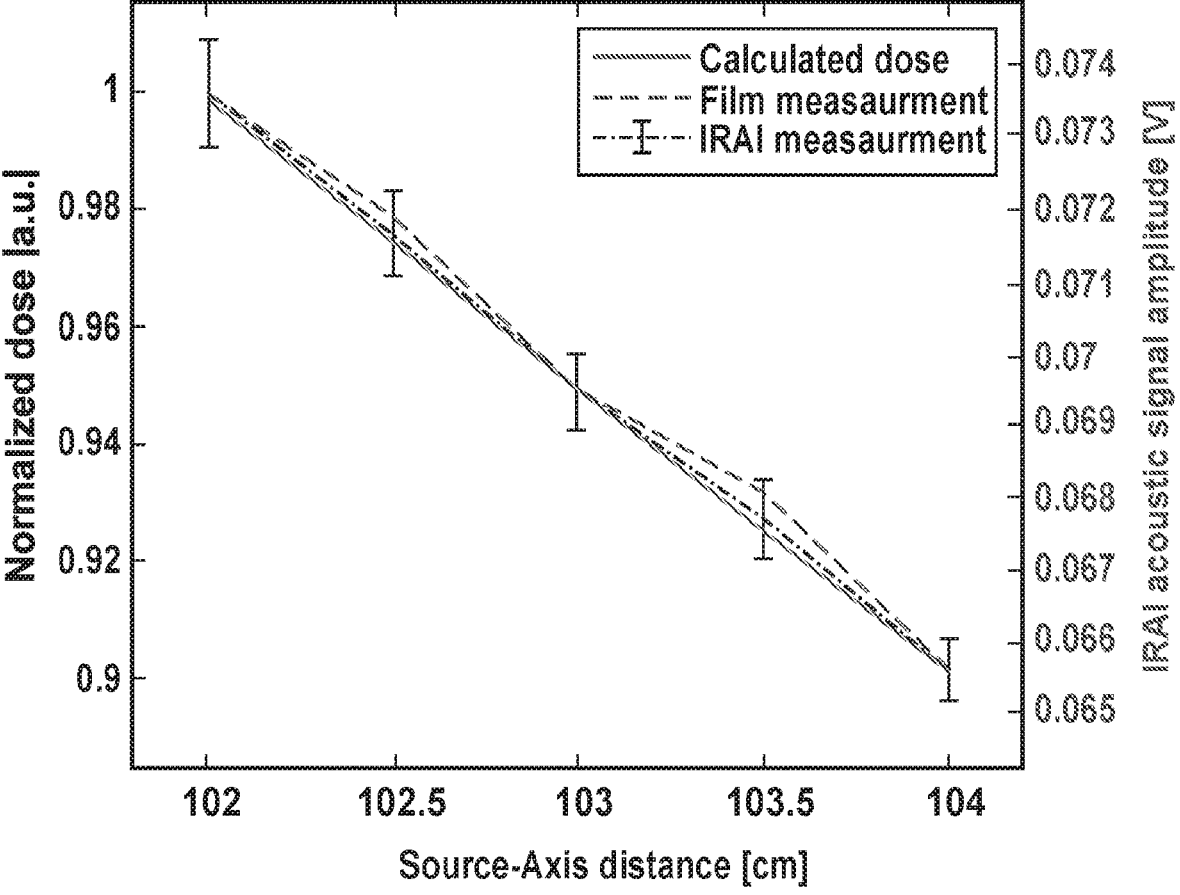
FIG. 21 is a plot of normalized dose vs SAD showing the dose sensitivity of iRAI dosimetry, in accordance with an example.

FIG. 21 is a plot of normalized dose vs SAD showing the dose sensitivity of iRAI dosimetry. FIG. 21 compares both the measured iRAI signal amplitude and the normalized dose per pulse derived from film dosimetry as a function of SAD. A dose fitting line based on the attenuation equation (i.e., the inverse square law) of electron beam in air was determined with the data of the linearity measurement shown in FIG. 20A. Although the slopes of the film measurement and the calculated dose as a function of SAD are the same, the film measurement shows some offsets at some SADs. The error bars of FIG. 21 represent the radiation acoustic measurement over 30 measurements at each SAD. The average value of the radiation acoustic measurements at each SAD is more consistent with the calculated dose than the film measurements are. The standard deviations of single pulse measurements averaged 0.79% over the five SAD positions. The average dose difference between each SAD increment was about 2.5% showing that the dose resolution of the iRAI method implemented by the system 1700 of FIG. 17 is less than 2.5%. By calculating the standard deviation of the iRAI signal amplitude at each SAD, a maximum standard deviation of 1% demonstrates that the uncertainty of radiation acoustic dosimetric measurement is less than 1%, which is within the clinical acceptable dose variation of 3%.

Figure 22:
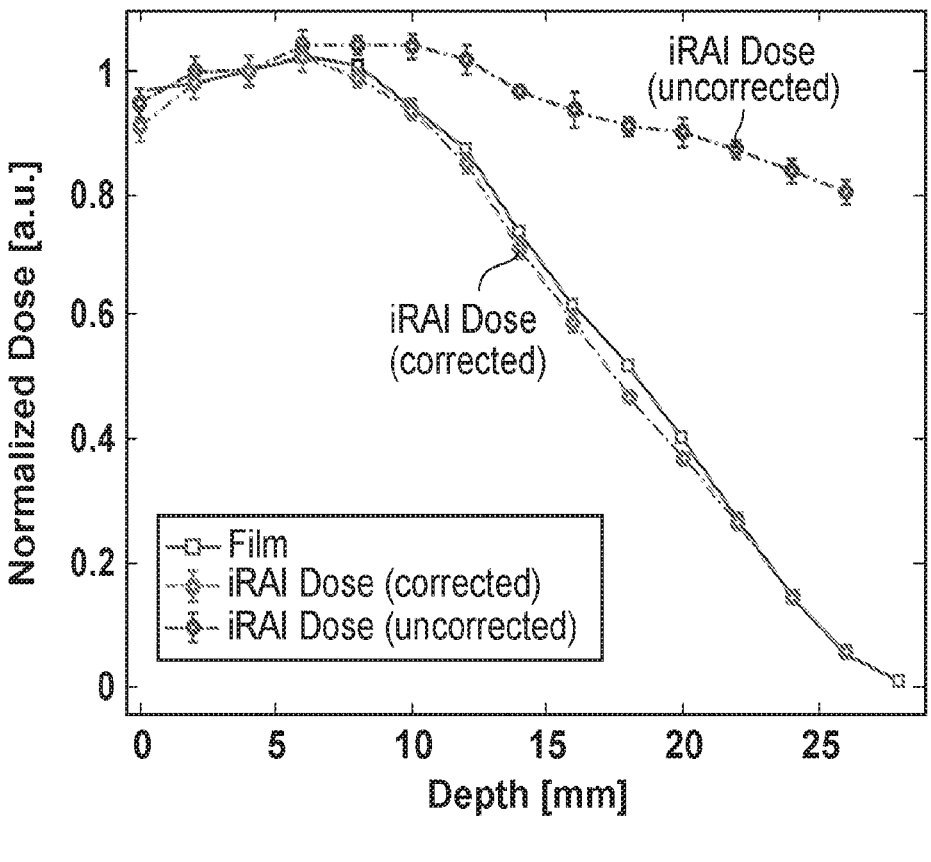
FIG. 22 is a plot of the normalized dose vs depth comparing the normalized depth dose measurements from both iRAI and film dosimetry, in accordance with an example.

FIG. 22 is a plot comparing the normalized depth dose measurements from both iRAI and film dosimetry. The data presented in FIG. 22 was taken using the system 1800 of FIG. 18. During the measurements, the depths for the irradiation beam were kept consistent between the iRAI and film measurements, including the 10 cm distance between the collimator and the surface of the phantom. The iRAI depth dose curve shows similar features as the film, such as a dose build up region, a maximum dose point, and a fall off region. The iRAI voltage versus dose relationship of FIG. 20B was used as a calibration curve for dose measurement. As electrons travel in the phantom, the spatial distribution of the electrons spreads out following a teardrop shape and the average energy of the electrons decreases. In order to correctly apply a calibration curve of the iRAI voltage vs dose relationship as a function of depth, a correction factor was used to compensate for the departure from the fixed measurement conditions of the calibration curve (i.e., altered beam size due to beam divergence, energy changes, transducer- to beam-center distance, and measurement depth in the phantom). The correction factor was determined by Monte Carlo simulated technique which considered the relative energy changing with depth as well as relative fluence changes, with respect to the calibration, as the beam diverges to account for deviations in measurement conditions compared to the calibration conditions at a fixed depth.

The red and blue curves (see labeling) correspond to the corrected and uncorrected normalized iRAI dose, respectively. The use of the correction factor improved the iRAI RSME, with respect to the film measurements, from 0.3774, for the uncorrected case, to 0.0243. At 26 mm the film measurement reaches a detection limit while the iRAI can still detect a relatively strong acoustical signal, which is also related to the relatively big focal zone of the transducer. Compared with the film measurement, the standard deviation of the iRAI signals at each depth are dominated by single pulse-to-pulse measurement fluctuations, which may result from either or both of the stability of data acquisition system as well as actual linac pulse to pulse variation. The film measurement had an average of 150 linac pulses delivered over the 500 ms of irradiation time while the iRAI measured each individual pulse. For direct dose measurements on patients, no current clinical dosimetry method exists for such deep tissue dosimetry without relying on superficial measurements.

Figures 23A, 23B, 23C, 23D, 23E:
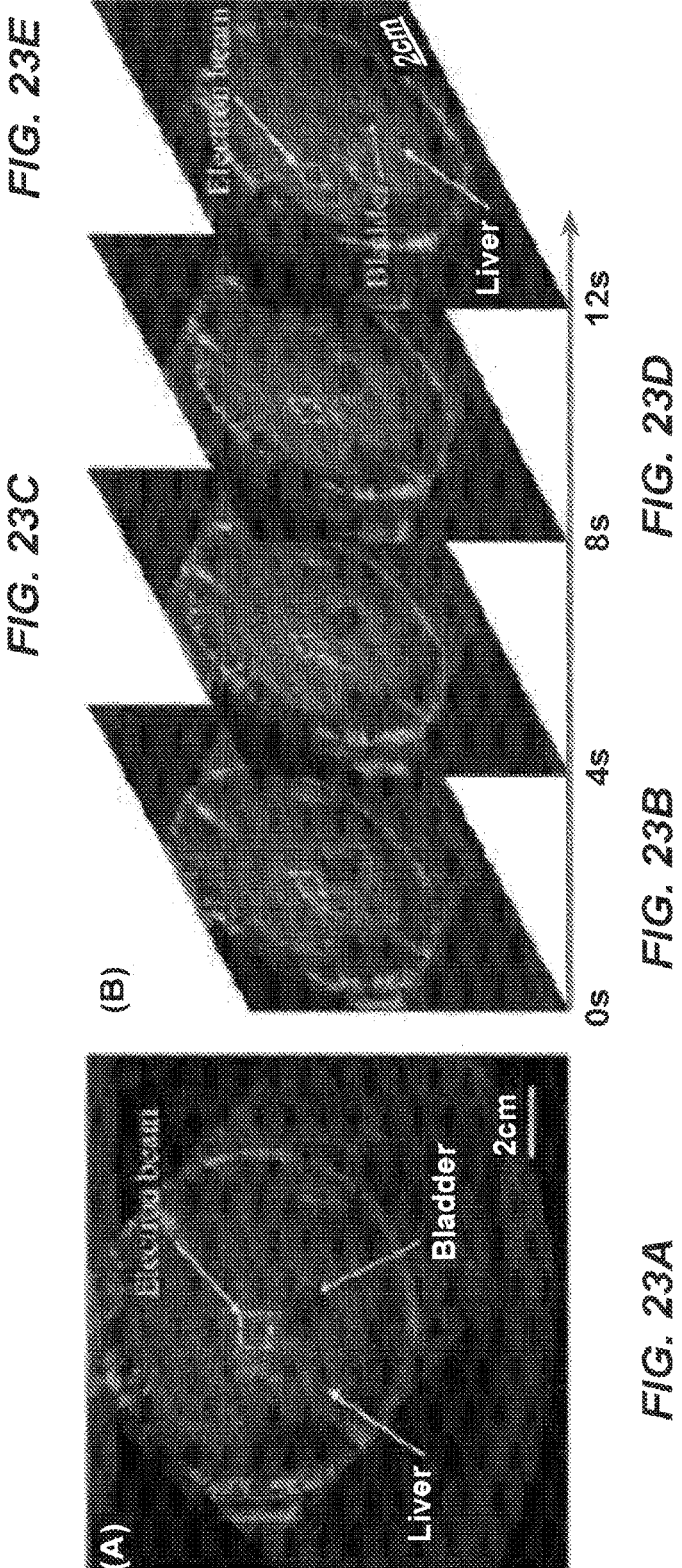
FIG. 23A is a registered and fused image of iRAI and US dual-modality imaging, in accordance with an example.
FIG. 23B is an iRAI and US dual-modality image of a rabbit liver model ex vivo at a time of 0 seconds, in accordance with an example.
FIG. 23C is an iRAI and US dual-modality image of a rabbit liver model ex vivo at a time of 4 seconds, in accordance with an example.
FIG. 23D is an iRAI and US dual-modality image of a rabbit liver model ex vivo at a time of 8 seconds, in accordance with an example.
FIG. 23E is an iRAI and US dual-modality image of a rabbit liver model ex vivo at a time of 12 seconds, in accordance with an example.

FIGS. 23A-23E are iRAI and US dual-modality images of a rabbit liver model ex vivo, such as the rabbit liver of the schematic 1900 of FIG. 19. FIG. 23A is a registered and fused image of iRAI and US dual-modality imaging, while FIGS. 23B-23E are multiple frames of the image of iRAI and US dual-modality imaging at different time points. The fused images of FIG. 23A were each acquired separately by one of the two orthogonally oriented probes as described in reference to FIG. 19. The iRAI image shows the boundary of the dose distribution in red, which shows that the probe's frequency bandwidth is primarily sensitive to the boundary of the dose deposition for the large of treatment field of FIG. 23A. The position of the delivered high dose rate electron beam is marked by the yellow dashed box, which corresponds well with the iRAI image. FIGS. 23B-23E are images of the rabbit liver as it was translated in one direction for 16.7 s during constant irradiation. During translation, the beam axis and probe position remained fixed. FIGS. 23B-23E show that the iRAI signal-to-noise ratio (SNR) during FLASH-RT dose rates is sufficiently high enough to allow for single linac pulse measurements. FIGS. 23B-23E illustrate that a frame rate of around 300 Hz is achievable, which is on the order of the linac repetition rate for the dual-modality imaging of the radiation beam location with respect to the soft tissue phantom.

In embodiments, a method for performing real-time dosimetry measurements for online adapted FLSH-RT may include positioning transducers relative to a target site or region of interest, with the transducers configured to receive signals from the target site. The method further includes irradiating the region of interest according to FLASH-RT parameters, dosages, and techniques. For example, a linac source may provide radiation of greater than 30 Gy/s, greater than 40 Gy/s, greater than 50 Gy/s, or another radiation dosage amount required for treatment of a tumor or target in a region of interest. Additionally, the irradiation may include one or more pulses, at least one pulse, 10 or fewer pulses, 20 or fewer pulses, 50 or fewer pulses, or 100 or fewer pulses. The pulses may have a period on the order of 100 microseconds, 1 millisecond, 10 milliseconds, less than ten milliseconds, or less than 100 milliseconds. In embodiments, the irradiation may include a single pulse. In embodiments, the irradiation may include pulses with widths on the order of 1 microsecond, tens of microseconds, hundreds of microseconds, or widths less than 100 microseconds, less than 50 microseconds, less than 10 microseconds, or less than 1 microsecond. In embodiments, the irradiation may include pulses with a duty cycle of less than 1%, from 1 to 10%, from 10% to 25%, from 25% to 50%, from 50% to 75%, or a duty cycle greater than 75%. Additionally, the pulse width may be determined by the pulse full width at half maximum (FWHM), half width at half maximum (HWHM), full duration at half maximum (FDHM), 90% of maximum amplitude width, a pulse width measurement from Euler's number and the pulse amplitude, or another pulse width measurement or definition.

One or more processors may be employed for controlling a radiation source (e.g., a linac) and for performing the steps of the methods described herein. The method further includes receiving, at transducers ionizing radiation acoustic and ultrasound signals from the region of interest and processing, by the one or more processors, the received signals from the region of interest. The one or more processors determining relative dosimetry imaging of the applied radiation and spatial imaging of tissue in the region of interest. The one or more processors further determine a property of tissue structures in the region of interest for further analysis. The property of the tissues structures may include a Grüneisen coefficient, tissue density, a thermal efficiency of the tissue, or another tissue property. The one or more processors then derive absolute dosimetry imaging from the relative dosimetry imaging, spatial mapping, and one or more properties of the tissue structures in the region of interest. The one or more processors then fuse the dosimetry imaging and spatial mapping of the region of interest, or tissue within the region of interest, and feedback is provided to the radiation source and the one or more processors update parameters for a next radiation dosage. The feedback may include a new set of spatial coordinates, or beam shaping parameters for providing radiation to a region of interest, and/or the updated feedback may include a new radiation dosage amount such as an increased dosage, a decreased dosage or substantially the same dosage amount as a compared to a previous radiation dosage. The described implementation of real time dosimetry and spatial mapping of dosage enables live and continuous tuning of dosage amount, and radiation targeting during an RT session. Specifically, the methods and systems described may be implemented for real time dosimetry during FLASH-RT providing a means for performing ultra-fast and ultra-high dose rate RT with live tuning during the therapy session. The continuous monitoring and tuning during FLASH-RT allows for more accurate application of radiation which may prevent unnecessary radiation of healthy tissues, and increased delivery of radiation to targets (e.g., tumors) in a region of interest resulting in more efficient delivery of radiation, and therefore, a more effective treatment of a cancer, tumor, or other target in the region of interest.

As previously discussed, FLASH-RT delivers the same dose as conventional RT in a fraction of a second using only a handful of linac pulses, whereas conventional RT requires many more pulses and therefore longer treatment times. The sub-second treatment capabilities of FLASH-RT result in a transient oxygen depletion effect, which is an essential feature for sparing normal tissue while maintaining the same efficacy in eradicating tumors. This results in approximately a 20-30% reported reduction in toxicity.

The data presented in FIGS. 20A, 20B, 21, 22, and 23 demonstrate the feasibility and accuracy of iRAI for real-time single radiation pulse deep tissue in vivo dosimetry during FLASH-RT as well real-time mapping of the dose deposition with respect to surrounding tissue which may enable safer FLASH-RT by preventing the treatment of healthy cells and increased targeting accuracy of target tumors or tissue regions. The disclosed systems and methods that utilize measurements of both US and iRAI signals allow for the real-time dosimetry and tuning of FLASH-RT and therefore address deficiencies of current dosimetry techniques for FLASH-RT.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

What is claimed is:

1. A method for adapted radiotherapy comprising:
receiving, at transducers, signals from a region of interest, the received signals comprising ionizing radiation acoustic signals and ultrasound signals, the ionizing radiation acoustic signals and the ultrasound signals being generated in response to radiation applied to the region of interest;
processing the received signals and determining relative dosimetry imaging of the radiation applied to the region of interest;
determining spatial imaging of tissue in the region of interest;
determining a property of tissue structures in the region of interest;
deriving absolute dosimetry imaging from the relative dosimetry imaging, spatial mapping, and property of tissue structures in the region of interest;
fusing the absolute dosimetry imaging and the spatial imaging of the tissue; and providing feedback to a radiation source and updating parameters for a next radiation dosage.

2. The method of claim 1, wherein the transducers are matrix array transducers.

3. The method of claim 1, wherein processing the received signals comprises filtering and amplifying the received signals.

4. The method of claim 1, wherein processing the received signals comprises performing beamforming on the signals.

5. The method of claim 1, wherein the spatial imaging of tissue in the region of interest comprises spatial imaging of a location of a tumor.

6. The method of claim 1, wherein the spatial imaging of tissues in the region of interest comprises spatial imaging of a location of healthy normal tissue.

7. The method of claim 1, wherein the spatial imaging of tissue in the region of interest comprises spatial imaging of a location of a tumor, healthy normal tissue, and any borders or boundaries between the tumor and healthy normal tissue.

8. The method of claim 1, wherein the property of tissue structures in the region of interest comprises a Grüneisen coefficient.

9. The method of claim 1, wherein the property of tissue structures in the region of interest comprises tissue density.

10. The method of claim 1, wherein the property of tissue structures in the region of interest comprises thermal efficiency of the tissue.

11. The method of claim 1, further comprising determining an attenuation of the ionizing radiation acoustic signals in the region of interest.

12. The method of claim 1, further comprising determining speed of sound in the region of interest.

13. The method of claim 1, further comprising determining stress and strain characteristics in the region of interest.

14. The method of claim 1, wherein providing feedback to the radiation source and updating parameters for the next radiation dosage comprises updating a radiation dosage amount.

15. The method of claim 1, wherein providing feedback to the radiation source and updating parameters for the next radiation dosage comprises updating a target location and shape of the applied radiation beam.

16. The method of claim 1, further comprising irradiating the region of interest according to FLASH radiotherapy irradiation dosages.

17. The method of claim 1, further comprising irradiating the region of interest comprises irradiating the region of interest with dosages of greater than 40 Gy/s.

* * * * *